(12) United States Patent
De Pedro Montejo et al.

(10) Patent No.: US 10,414,745 B2
(45) Date of Patent: Sep. 17, 2019

(54) PHENOL DERIVATIVES TO TREAT CANCER

(71) Applicant: FUNDACIÓN MEDINA. CENTRO DE EXCELENCIA EN INVESTIGACIÓN DE MEDICAMENTOS INNOVADORES EN ANDALUCÍA, Granada (ES)

(72) Inventors: Nuria De Pedro Montejo, Madrid (ES); Victor Gonzalez Menendez, Granada (ES); Gloria Crespo Sueiro, Madrid (ES); Ignacio Perez-Victoria Moreno De Barreda, Granada (ES); Bastien Cautain, Armilla-Granada (ES); Maria Francisca Vicente Perez, Madrid (ES); Jose Fernando Reyes Benitez, Gojar-Granada (ES); Olga Genilloud Rodriguez, Madrid (ES); Carmen Grinan Lison, Granada (ES); Juan Antonio Marchal Corrales, Granada (ES)

(73) Assignee: FUNDACIÓN MEDINA. CENTRO DE EXCELENCIA EN INVESTIGACIÓN DE MEDICAMENTOS INNOVADORES EN ANDALUCÍA, Granada (ES)

( * ) Notice: Subject to any disclaimer, the term of this patent is extended or adjusted under 35 U.S.C. 154(b) by 0 days.

(21) Appl. No.: 15/570,348

(22) PCT Filed: Apr. 29, 2016

(86) PCT No.: PCT/EP2016/059650
§ 371 (c)(1),
(2) Date: Oct. 29, 2017

(87) PCT Pub. No.: WO2016/174226
PCT Pub. Date: Nov. 3, 2016

(65) Prior Publication Data
US 2018/0148427 A1 May 31, 2018

(30) Foreign Application Priority Data
Apr. 30, 2015 (EP) .................................... 15382217

(51) Int. Cl.
| A61P 35/00 | (2006.01) |
| C12P 7/24 | (2006.01) |
| C12P 7/26 | (2006.01) |
| C12P 17/06 | (2006.01) |
| C07D 311/02 | (2006.01) |
| C07D 311/04 | (2006.01) |
| C07D 311/22 | (2006.01) |
| C07D 311/58 | (2006.01) |
| C07D 311/82 | (2006.01) |
| C07D 311/86 | (2006.01) |
| C07C 49/86 | (2006.01) |
| C12R 1/645 | (2006.01) |
| C07C 49/248 | (2006.01) |
| C07C 49/255 | (2006.01) |

(52) U.S. Cl.
CPC ............ *C07D 311/86* (2013.01); *A61P 35/00* (2018.01); *C07C 49/248* (2013.01); *C07C 49/255* (2013.01); *C07C 49/86* (2013.01); *C07D 311/02* (2013.01); *C07D 311/04* (2013.01); *C07D 311/22* (2013.01); *C07D 311/58* (2013.01); *C07D 311/82* (2013.01); *C12P 7/24* (2013.01); *C12P 7/26* (2013.01); *C12P 17/06* (2013.01); *C12R 1/645* (2013.01)

(58) Field of Classification Search
CPC ..... A61P 35/00; C07C 49/428; C07C 49/255; C07C 49/86; C07D 311/02; C07D 311/04; C07D 311/22; C07D 311/58; C07D 311/82; C12P 7/24; C12P 7/26; C12P 17/06; C12K 1/645
See application file for complete search history.

(56) References Cited

FOREIGN PATENT DOCUMENTS

JP 7-61950 3/1995

OTHER PUBLICATIONS

Wachi et al., JP 07061950 A (CAS Abstract) (Year: 1995).*
Roberts, et al., "Targeting the RAF-MEK-ERK mitogen-acativated protein kinase cascade for the treatment of cancer", Oncogene (2007) 26, 3291-3310.

(Continued)

*Primary Examiner* — Timothy R Rozof
(74) *Attorney, Agent, or Firm* — Kramer Amado, P.C.

(57) ABSTRACT

The present invention relates to compounds of general formula (I)

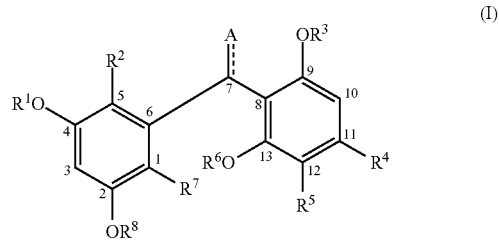

(I)

wherein $R^1$-$R^8$ take various meanings, pharmaceutical compositions containing them and their use in medicine, particularly for the treatment and/or prophylaxis of cancer.

21 Claims, 8 Drawing Sheets

(56) References Cited

OTHER PUBLICATIONS

Seo, "Cytotoxic Prenylated Xanthones and the Unusual Compounds Anthraquinobenzophenones from Cratoxylum sumatranum", J. Nat. Prod. 2002, 65, 299-305.
Xin, et al., "Two New Xanthones from Hypericum sampsonii and Biological Activity of the Isolated Compounds", Phytotherapy Research 25:536-539 (2011).
Yap, et al., "Small Molecule Inhibitors of the ERK Signaling Pathway: Towards Novel Anticancer Therapeutics", CHEMMEDCHEM 2011, 6, 38-48.

* cited by examiner

PHENOL DERIVATIVES TO TREAT CANCER

FIELD OF THE INVENTION

The present invention relates to new compounds, pharmaceutical compositions containing them and their use in medicine, particularly as agents able to treat cancer and/or prevent cancer. The present invention also relates to processes for preparing such compounds and compositions.

BACKGROUND OF THE INVENTION

Mitogen-activated protein kinase (MAPK) cascades are key signaling pathways involved in the regulation of normal cell proliferation, survival and differentiation. Aberrant regulation of MAPK cascades contributes to cancer and other human diseases. In particular, the extracellular signal-regulated kinase (ERK) MAPK pathway has been the subject of intense research scrutiny leading to the development of pharmacologic inhibitors for the treatment of cancer.

In the MAPK/ERK pathway (also known as the Ras-Raf-MEK-ERK pathway) the signal starts when a signaling molecule binds to receptor tyrosine kinases (RTKs), leading to the activation of Ras proteins. Subsequently, a three-stage phosphorylation cascade takes place: activated Ras activates the protein kinase activity of Raf serine/threonine kinases, and Raf kinase then activates the MAP/ERK kinase 1 and 2 (MEK1/2) dual-specificity protein kinases, which in turn activate ERK1/2 (Robert P J and Der C J Oncogene 2007).

There is now considerable evidence that links dysregulation of the Ras/Raf/MEK/ERK pathway to oncogenesis in humans. Ras is hyperactivated in around 30% of human cancers, most commonly the K-Ras isoform. More specifically, Ras-activating mutations have been reported in about 90% of pancreatic carcinomas, 50% of colon carcinomas, 30% of lung cancers, and in around 30% of myeloid leukemia cases. Activating mutations of Raf have also been reported in around 7% of human cancers. In particular, mutations of B-RAF have been observed in over 60% of melanomas, around 30% of ovarian cancer cases, and in approximately 20% of colorectal carcinomas, as well as in several other malignancies at lower frequencies. Constitutively active MEK1/2 and ERK1/2 proteins are present in a relatively high number of human tumors, particularly those from the colon, lung, pancreas, ovary and kidney (Yap, J L et al. Chem Med Chem 2011).

A number of MAPK/ERK pathway inhibitors have been developed and are being evaluated in preclinical studies and in early clinical trials.

Therefore, the provision of new inhibitors of this pathway presents both a great therapeutic opportunity and a tremendous challenge for cancer therapy.

BRIEF DESCRIPTION OF THE INVENTION

The present invention solves the aforementioned need by the provision of new compounds able to inhibit the Ras/Raf/MEK/ERK pathway.

In one aspect, the present invention is directed to compounds of general formula (I) or pharmaceutically acceptable salts, stereoisomers or solvates thereof (carbon atom numbering is shown in some instances for clarity purposes)

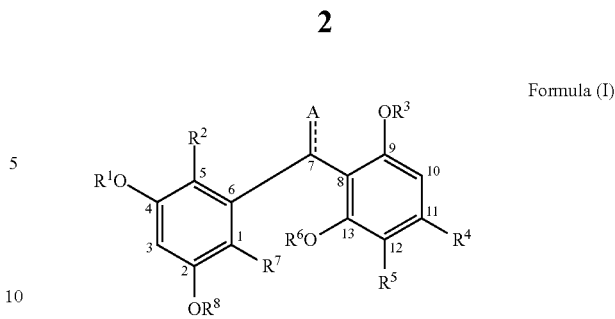

Formula (I)

wherein

----- A represents =O or OH;

$R^1$ is hydrogen or a hydroxyl protecting group and $R^2$ is selected from

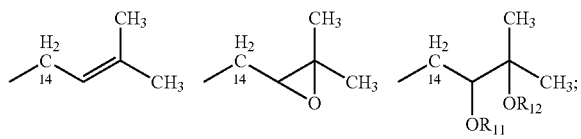

or $R^1$ and $R^2$ together form a ring selected from

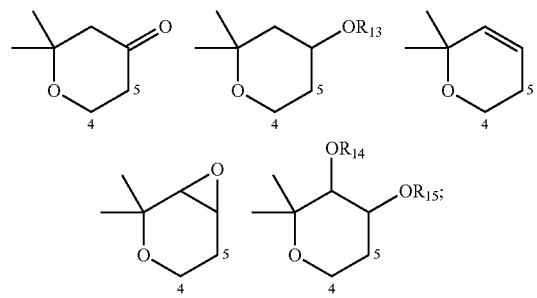

$R^3$ is hydrogen or a hydroxyl protecting group;

$R^4$ is methyl;

$R^5$ is hydrogen or halogen;

$R^6$ is hydrogen or a hydroxyl protecting group and $R^7$ is CHO or $CH_2(OH)$;

or $R^6$ and $R^7$ together form a single bond;

$R^8$ is hydrogen or a hydroxyl protecting group;

$R^{11}$, $R^{12}$, $R^{13}$, $R^{14}$ and $R^{15}$ independently represent hydrogen or a hydroxyl protecting group;

with the proviso that the compound 2,3',5',6-tetrahydroxy-2'-formyl-6'-(3-methyl-2-butenyl)-4-methyl-benzophenone is not included.

JP H0761950A relates to benzophenone derivatives having testosterone 5 alpha-reductase-inhibitory activity, which are useful as UV light absorbers for hair cosmetic compositions, and particularly discloses the compound 2,3',5',6-tetrahydroxy-2'-formyl-6'-(3-methyl-2-butenyl)-4-methyl-benzophenone (or 2-(2,6-dihydroxy-4-methyl-benzoyl)-4,6-dihydroxy-3-(3-methyl-but-2-enyl)-benzaldehyde), which is identified in said document as SB87-H and corresponds to the compound herein referred as MDN-0090, the chemical formula of which is depicted below

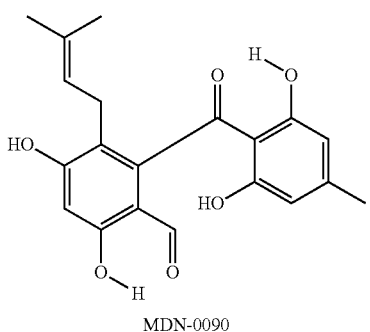 [SMILES: CC(C)=CCc1c(O)cc(O)c(C=O)c1C(=O)c1c(O)cc(C)cc1O]

MDN-0090

Accordingly, MDN-0090 is not claimed in this application as such; however, MDN-0090 is included in formula (I) for the rest of aspects of the invention indicated hereinafter, related to a medicament or pharmaceutical composition comprising compounds of formula (I), their use in medicine and particularly in treating and/or preventing cancer and processes for preparing such compounds and compositions.

Another aspect of this invention refers to a medicament or pharmaceutical composition comprising at least one compound of formula (I) as defined above, or a pharmaceutically acceptable salt, stereoisomer or solvate thereof and a pharmaceutically acceptable excipient Another aspect of this invention refers to a compound of formula (I) as defined above, or a pharmaceutically acceptable salt, stereoisomer or solvate thereof for use in medicine, particularly for the treatment and/or prophylaxis of cancer.

Another aspect of this invention refers to the use of a compound of formula (I) as defined above, or a pharmaceutically acceptable salt, stereoisomer or solvate thereof in the manufacture of a medicament for the treatment and/or prophylaxis of cancer.

Another aspect of the present invention refers to a method for the treatment and/or prophylaxis of cancer, the method comprising administering to the subject in need of such a treatment or prophylaxis an effective amount of a compound of formula (I) as defined above, or a pharmaceutically acceptable salt, stereoisomer or solvate thereof.

Thus, the present invention establishes that compounds of general formula (I) or pharmaceutically acceptable salts, stereoisomers or solvates thereof inhibit Ras/Raf/MEK/ERK pathway. The compounds of the invention have been found to exhibit inhibition activity in Ras/Raf/MEK/ERK pathway for different cancer treatments.

The present invention also relates to the obtention of compounds of formula (I) from microorganisms capable of producing them, specifically from a fungus identified as *Onychocola* sp., and more specifically from the strain of *Onychocola* sp. CBS 139230, and the formation of derivatives from the obtained compounds. In a preferred embodiment, the process for obtaining compounds of formula (I) comprises the steps of cultivating a strain of a microorganism capable of producing them such as *Onychocola* sp. CBS 139230 in an aqueous nutrient medium with assimilable carbon and nitrogen sources and salts, under controlled submerged aerobic conditions, and then recovering and purifying the compounds according to the invention from the culture broth.

Another aspect of the invention is the strain of *Onychocola* sp. with accession number CBS 139230.

These and other aspects of the invention will be apparent from and elucidated with reference to the embodiments described hereinafter.

DETAILED DESCRIPTION OF THE INVENTION

Figure 1:
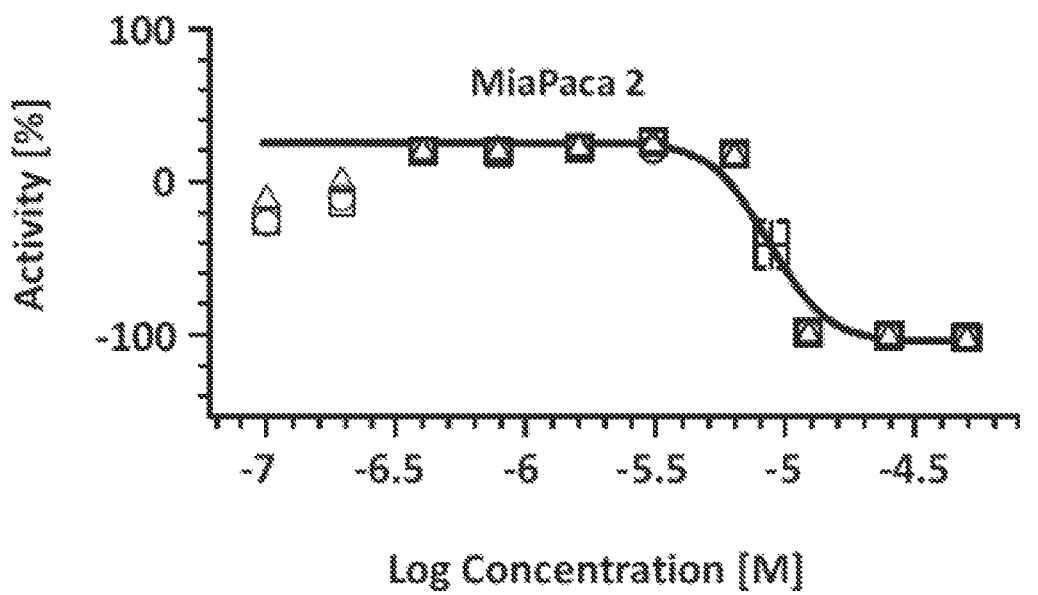
FIG. 1. Results of MTT assay in MiaPaca_2 and BxPC3 cell lines (i.e. growth inhibitory effect on tumoral pancreatic cell lines) at 72 hours of incubation with compound MDN-0090. See example 6.
Figure 1:
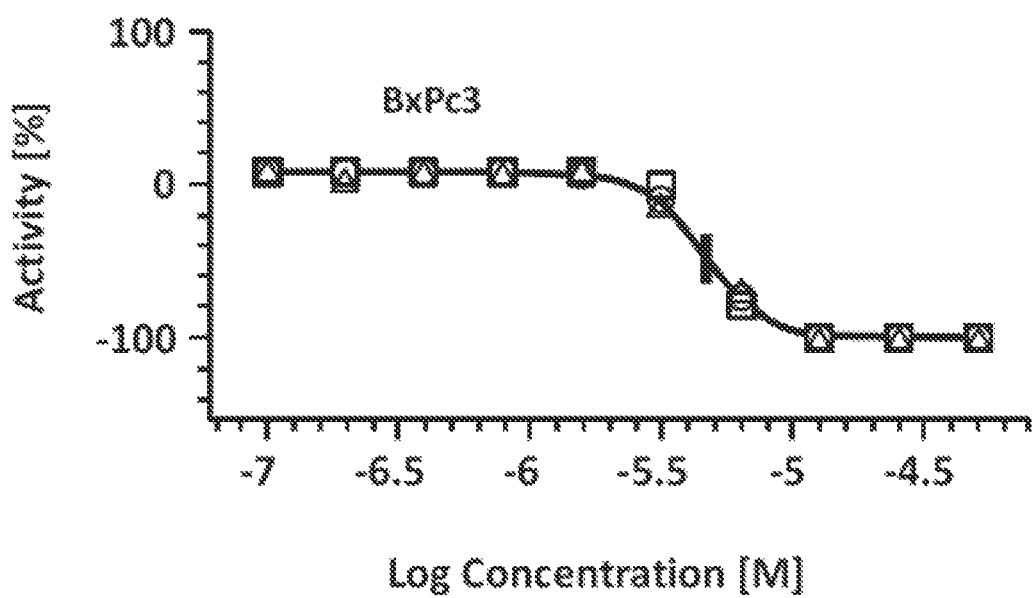

Cancer is a leading cause of human death, and it is fundamentally attributable to dysfunctional cell signaling. The Ras/Raf/MEK/ERK pathway can transmit signals, which result in the prevention or induction of apoptosis or cell cycle progression. Thus, it is an appropriate pathway to target for therapeutic intervention. Efforts to develop anticancer drugs have therefore focused, in great part, on identifying Ras/Raf/MEK/ERK pathway inhibitors.

The present invention relates to novel compounds able to treat and/or prevent cancer. These compounds, of general formula (I), are particularly useful as inhibitors of the Ras/Raf/MEK/ERK pathway.

In these compounds the groups can be selected in accordance with the following guidance:

Alkyl groups may be branched or unbranched, and preferably have from 1 to about 18 carbon atoms, such as from 1 to about 12 carbon atoms. One more preferred class of alkyl groups has from 1 to about 6 carbon atoms; even more preferred are alkyl groups having 1, 2, 3 or 4 carbon atoms. Methyl, ethyl, n-propyl, iso-propyl and butyl, including n-butyl, tert-butyl, sec-butyl and iso-butyl are particularly preferred alkyl groups in the compounds of the present invention. As used herein, the term alkyl, unless otherwise stated, refers to both cyclic and non-cyclic groups, although cyclic groups will comprise at least three carbon ring members.

Alkenyl and alkynyl groups in the compounds of the present invention may be branched or unbranched, have one or more unsaturated linkages and from 2 to about 18 carbon atoms, such as from 2 to about 12 carbon atoms. One more preferred class of alkenyl and alkynyl groups has from 2 to about 6 carbon atoms; even more preferred are alkenyl and alkynyl groups having 2, 3 or 4 carbon atoms. The terms alkenyl and alkynyl as used herein refer to both cyclic and noncyclic groups, although cyclic groups will comprise at least three carbon ring members.

Suitable aryl groups in the compounds of the present invention include single and multiple ring compounds, including multiple ring compounds that contain separate and/or fused aryl groups. Typical aryl groups contain from 1 to 3 separated and/or fused rings and from 6 to about 18 carbon ring atoms. Preferably aryl groups contain from 6 to about 10 carbon ring atoms. Specially preferred aryl groups include substituted or unsubstituted phenyl, substituted or unsubstituted naphthyl, substituted or unsubstituted biphenyl, substituted or unsubstituted phenanthryl and substituted or unsubstituted anthryl.

The groups above mentioned may be substituted at one or more available positions by one or more suitable groups such as OR', =O, SR', SOR', $SO_2R'$, $OSO_2R'$, $OSO_3R'$, $NO_2$, NHR', $N(R')_2$, =N—R', N(R')COR', $N(COR')_2$, N(R')$SO_2R'$, N(R')C(=NR')N(R')R', CN, halogen, COR', COOR', OCOR', OCOOR', OCONHR', $OCON(R')_2$, CONHR', $CON(R')_2$, CON(R')OR', $CON(R')SO_2R'$, $PO(OR')_2$, PO(OR')R', PO(OR')(N(R')R'), substituted or unsubstituted $C_1$-$C_{12}$ alkyl, substituted or unsubstituted $C_2$-$C_{12}$ alkenyl, substituted or unsubstituted $C_2$-$C_{12}$ alkynyl, and substituted or unsubstituted aryl, wherein each of the R' groups is independently selected from the group consisting of hydrogen, OH, $NO_2$, $NH_2$, SH, CN, halogen, COH, COalkyl, COOH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, and substituted or unsubstituted aryl. Where such groups are themselves substituted, the substituents may be chosen from the foregoing list.

Suitable halogen groups or substituents in the compounds of the present invention include F, Cl, Br, and I.

Suitable protecting groups are well known for the skilled person in the art. A general review of protecting groups in organic chemistry is provided by Wuts, PGM and Greene T W in Protecting Groups in Organic Synthesis, $4^{th}$ Ed. Wiley-Interscience, and by Kocienski P J in Protecting Groups, $3^{rd}$ Ed. Georg Thieme Verlag. These references provide sections on protecting groups for hydroxy groups. All these references are incorporated by reference in their entirety.

Examples of such protected OH include ethers, silyl ethers, esters, sulfonates, sulfenates and sulfinates, carbonates and carbamates. In the case of ethers the protecting group for the OH can be selected from methyl, methoxymethyl, methylthiomethyl, (phenyldimethylsilyl)methoxymethyl, benzyloxymethyl, p-methoxybenzyloxymethyl, [(3,4-dimethoxybenzyl)oxy]methyl, p-nitrobenzyloxymethyl, o-nitrobenzyloxym ethyl, [(R)-1-(2-nitrophenyl)ethoxy] methyl, (4-methoxyphenoxy)methyl, guaiacolmethyl, [(p-phenylphenyl)oxy]methyl, t-butoxymethyl, 4-pentenyloxymethyl, siloxymethyl, 2-methoxyethoxymethyl, 2-cyanoethoxymethyl, bis(2-chloroethoxy)methyl, 2,2,2-trichloroethoxymethyl, 2-(trimethylsilyl)ethoxymethyl, menthoxymethyl, o-bis(2-acetoxyethoxy)methyl, tetrahydropyranyl, fluorous tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-dioxide, 1-[(2-chloro-4-methyl)phenyl]-4-methoxypiperidin-4-yl, 1-(2-fluorophenyl)-4-methoxypiperidin-4-yl, 1-(4-chlorophenyl)-4-methoxypiperidin-4-yl, 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 2-hydroxyethyl, 2-bromoethyl, 1-[2-(trimethylsilypethoxy]ethyl, 1-methyl-1-methoxyethyl, 1-methyl-1-benzyloxyethyl, 1-methyl-1-benzyloxy-2-fluoroethyl, 1-methyl-1-phenoxyethyl, 2,2,2-trichloroethyl, 1,1-dianisyl-2,2,2-trichloroethyl, 1,1,1,3,3,3-hexafluoro-2-phenylisopropyl, 1-(2-cyanoethoxy)ethyl, 2-trimethylsilylethyl, 2-(benzylthio)ethyl, 2-phenylselenyl) ethyl, t-butyl, cyclohexyl, 1-methyl-1'-cyclopropylmethyl, allyl, prenyl, cinnamyl, 2-phenallyl, propargyl, p-chlorophenyl, p-methoxyphenyl, p-nitrophenyl, 2,4-dinitrophenyl, 2,3,5,6-tetrafluoro-4-(trifluoromethyl)phenyl, benzyl, p-methoxybenzyl, 3,4-dimethoxybenzyl, 2,6-dimethoxybenzyl, o-nitrobenzyl, p-nitrobenzyl, pentadienylnitrobenzyl, pentadienylnitropiperonyl, halobenzyl, 2,6-dichlorobenzyl, 2,4-dichlorobenzyl, 2,6-difluorobenzyl, p-cyanobenzyl, fluorous benzyl, 4-fluorousalkoxybenzyl, trimethylsilylxylyl, p-phenylbenzyl, 2-phenyl-2-propyl, p-acylaminobenzyl, p-azidobenzyl, 4-azido-3-chlorobenzyl, 2-trifluoromethylbenzyl, 4-trifluoromethylbenzyl, p-(methylsulfinyl)benzyl, p-siletanylbenzyl, 4-acetoxybenzyl, 4-(2-trimethylsilyl)ethoxymethoxybenzyl, 2-naphthylmethyl, 2-picolyl, 4-picolyl, 3-methyl-2-picolyl N-oxide, 2-quinolinylmethyl, 6-methoxy-2-(4-methylphenyl-4-quinolinemethyl, 1-pyrenylmethyl, diphenylmethyl, 4-methoxydiphenylmethyl, 4-phenyldiphenylmethyl, p,p'-dinitrobenzhydryl, 5-dibenzosuberyl, triphenylmethyl, tris(4-t-butylphenyl) methyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxy) phenyldiphenylmethyl, 4,4',4"-tris(4,5-dichlorophthalimidophenyl)methyl, 4,4',4"-tris (levulinoyloxyphenyl)methyl, 4,4',4"-tris (benzoyloxyphenyl)methyl, 4,4'-dimethoxy-3"-[N-(imidazolylmethyl)]trityl, 4,4'-dimethoxy-3"-[N-(imidazolylethyl)carbamoyl]trityl, bis(4-methoxyphenyl)-1'-pyrenylmethyl, 4-(17-tetrabenzo[a,c,g,i] fluorenylmethyl)-4,4"-dimethoxytrityl, 9-anthryl, 9-(9-phenyl)xanthenyl, 9-phenylthioxanthyl, 9-(9-phenyl-10-oxo)anthryl, 1,3-benzodithiolan-2-yl, and 4,5-bis (ethoxycarbonyl)[1,3]-dioxolan-2-yl, benzisothiazolyl S,S-dioxido. In the case of silyl ethers the protecting group for the OH can be selected from trimethylsilyl, triethylsilyl, triisopropylsilyl, dimethylisopropylsilyl, diethylisopropylsilyl, dimethylhexylsylil, 2-norbornyldimethylsilyl, t-butyldimethylsilyl, t-butyldiphenylsilyl, tribenzylsilyl, tri-p-xylylsilyl, triphenylsilyl, diphenylmethylsilyl, di-t-butylmethylsilyl, bis(t-butyl)-1-pyrenylmethoxysilyl, tris (trimethylsilyl)silyl, (2-hydroxystyryl)dimethylsilyl, (2-hydroxystyryl)diisopropylsilyl, t-butylmethoxyphenylsilyl, t-butoxydiphenylsilyl, 1,1,3,3-tetraisopropyl-3-[2-(triphenylmethoxy)ethoxy]disiloxane-1-yl, and fluorous silyl. In the case of esters the protecting group for the OH can be selected from formate, benzoylformate, acetate, chloroacetate, dichloroacetate, trichloroacetate, trichloroacetamidate, trifluoroacetate, methoxyacetate, triphenylmethoxyacetate, phenoxyacetate, p-chlorophenoxyacetate, phenylacetate, diphenylacetate, 3-phenylpropionate, bis-fluorous chain type propanoyl, 4-pentenoate, 4-oxopentanoate, 4,4-(ethylenedithio)pentanoate, 5[3-bis(4-methoxyphenyl)hydroxymethylphenoxy]levulinate, pivaloate, 1-adamantoate, crotonate, 4-methoxycrotonate, benzoate, p-phenylbenzoate, 2,4,6-trimethylbenzoate, 4-bromobenzoate, 2,5-difluorobenzoate, p-nitrobenzoate, picolinate, nicotinate, 2-(azidomethyl)benzoate, 4-azidobutyrate, (2-azidomethyl)phenylacetate, 2-{[(tritylthio)oxy]methyl}benzoate, 2-{[(4-methoxytritylthio)oxy] methyl}benzoate, 2-{[methyl(tritylthio)amino] methyl}benzoate, 2-{{[(4-methoxytrityl)thio] methylamino}-methyl}benzoate, 2-(allyloxy)phenylacetate, 2-(prenyloxymethyl)benzoate, 6-(levulinyloxymethyl)-3-methoxy-2-nitrobenzoate, 6-(levulinyloxymethyl)-3-methoxy-4-nitrobenzoate, 4-benzyloxybutyrate, 4-trialkylsilyloxybutyrate, 4-acetoxy-2,2-dimethylbutyrate, 2,2-dimethyl-4-pentenoate, 2-iodobenzoate, 4-nitro-4-methylpentanoate, o-(dibromomethyl)benzoate, 2-formylbenzenesulfonate, 4-(methylthiomethoxy)butyrate, 2-(methylthiomethoxymethyl)benzoate, 2-(chloroacetoxymethyl)benzoate, 2-[(2-chloroacetoxy)ethyl]benzoate, 2-[2-(benzyloxy)ethyl]benzoate, 2-[2-(4-methoxybenzyloxy)ethyl]benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N,N-tetramethylphosphorodiamidate, and 2-chlorobenzoate. In the case of sulfonates, sulfenates and sulfinates the protecting group for the OH can be selected from sulfate, allylsulfonate, methanesulfonate, benzylsulfonate, tosylate, 2-[(4-nitrophenyl)ethyl]sulfonate, 2-trifluoromethylbenzenesulfonate, 4-monomethoxytritylsulfenate, alkyl 2,4-dinitrophenylsulfenate, 2,2,5,5-tetramethylpyrrolidin-3-one-1-sulfinate, borate, and dimethylphosphinothiolyl. In the case of carbonates the protecting group for the OH can be selected from methyl carbonate, methoxymethyl carbonate, 9-fluorenylmethyl carbonate, ethyl carbonate, bromoethyl carbonate, 2-(methylthiomethoxy)ethyl carbonate, 2,2,2-trichloroethyl carbonate, 1,1-dimethyl-2,2,2-trichloroethyl carbonate, 2-(trimethylsilyl)ethyl carbonate, 2-[dimethyl(2-naphthylmethyl)silyl]ethyl carbonate, 2-(phenylsulfonyl) ethyl carbonate, 2-(triphenylphosphonio)ethyl carbonate, cis-[4-[[(methoxytrityl)sulfenyl]oxy]tetrahydrofuran-3-yl]oxy carbonate, isobutyl carbonate, t-butyl carbonate, vinyl carbonate, allyl carbonate, cinnamyl carbonate, propargyl carbonate, p-chlorophenyl carbonate, p-nitrophenyl carbonate, 4-ethoxy-1-naphthyl carbonate, 6-bromo-7-hydroxycoumarin-4-ylmethyl carbonate, benzyl carbonate, o-nitrobenzyl carbonate, p-nitrobenzyl carbonate, p-methoxybenzyl carbonate, 3,4-dimethoxybenzyl carbonate, anthraquinon-2-ylmethyl carbonate, 2-dansylethyl carbonate, 2-(4-nitrophenyl)ethyl carbonate, 2-(2,4-dinitrophenyl)ethyl carbonate, 2-(2-nitrophenyl)propyl carbonate, alkyl 2-(3,4-methylenedioxy-6-nitrophenyl)propyl carbonate, 2-cyano-1-phenylethyl carbonate, 2-(2-pyridyl)amino-1-phenylethyl carbonate, 24N-methyl-N-(2-pyridyl)]amino-1-phenylethyl carbonate, phenacyl carbonate, 3',5'-dimethoxybenzoin carbonate, methyl dithiocarbonate, and S-benzyl thiocarbonate. And in the case of carbamates the protecting group for the OH can be selected from dimethylthiocarbamate, N-phenylcarbamate, N-methyl-N-(o-nitrophenyl)carbamate. The mention of these groups should be not interpreted as a limitation of the scope of the invention, since they have been mentioned as a mere illustration of protecting groups for OH, but further groups having said function may be known by the skilled person in the art, and they are to be understood to be also encompassed by the present invention.

The term "salt" is to be understood as meaning any form of the active compound according to the invention in which this assumes an ionic form or is charged and is coupled with a counter-ion (a cation or anion) or is in solution. By this are also to be understood complexes of the active compound with other molecules and ions, in particular complexes which are complexed via ionic interactions. The definition includes in particular physiologically acceptable salts; this term must be understood as equivalent to "pharmacologically acceptable salts" or "pharmaceutically acceptable salts".

The term "physiologically acceptable salt" or "pharmaceutically acceptable salt" is understood in particular, in the context of this invention, as a salt (as defined above) formed either with a physiologically tolerated acid, that is to say salts of the particular active compound with inorganic or organic acids which are physiologically tolerated—especially if used on humans and/or mammals—or with at least one, preferably inorganic, cation which are physiologically tolerated—especially if used on humans and/or mammals. Examples of physiologically tolerated salts of particular acids are salts of: hydrochloric acid, hydrobromic acid, sulfuric acid, hydrobromide, monohydrobromide, monohydrochloride or hydrochloride, methiodide, methanesulfonic acid, formic acid, acetic acid, oxalic acid, succinic acid, malic acid, tartaric acid, mandelic acid, fumaric acid, lactic acid, citric acid, glutamic acid, hippuric acid, picric acid and/or aspartic acid. Examples of physiologically tolerated salts of particular bases are salts of alkali metals and alkaline earth metals and with $NH_4$.

For those persons skilled in the art, it will be evident that the scope of the present invention also includes salts which are not pharmaceutically acceptable as possible means for obtaining pharmaceutically acceptable salts.

The term "solvate" according to this invention is to be understood as meaning any form of the compound according to the invention in which this compound has attached to it via non-covalent binding another molecule (most likely a polar solvent) especially including hydrates and alcoholates, e.g. methanolate. Methods of solvation are generally known within the art. The compounds of the invention may present different polymorphic forms, and it is intended that the invention encompasses all such forms.

Any compound referred to herein is intended to represent such specific compound as well as certain variations or forms. The compounds of the present invention represented by the above described formula (I) include stereoisomers. The term "stereoisomer" as used herein includes any enantiomer, diastereomer or geometric isomer (E/Z) of such compound. In particular, compounds referred to herein may have asymmetric centres and therefore exist in different enantiomeric or diastereomeric forms. Thus any given compound referred to herein is intended to represent any one of a racemate, one or more enantiomeric forms, one or more diastereomeric forms, and mixtures thereof. Likewise, stereoisomerism or geometric isomerism related to a double bond is also possible, therefore in some cases the molecule could exist as (E)-isomer or (Z)-isomer (trans and cis isomers). If the molecule contains several double bonds, each double bond will have its own stereoisomerism, that could be the same or different than the stereoisomerism of the other double bonds of the molecule. All the stereoisomers including enantiomers, diastereoisomers and geometric isomers of the compounds referred to herein, and mixtures thereof, are considered within the scope of the present invention.

Furthermore, any compound referred to herein may exist as tautomers. Specifically, the term tautomer refers to one of two or more structural isomers of a compound that exist in equilibrium and are readily converted from one isomeric form to another. Common tautomeric pairs are enamine-imine, amide-imidic acid, keto-enol, lactam-lactim, etc.

Unless otherwise stated, the compounds of the invention are also meant to include isotopically-labelled forms i.e. compounds which differ only in the presence of one or more isotopically-enriched atoms. For example, compounds having the present structures except for the replacement of at least one hydrogen atom by a deuterium or tritium, or the replacement of at least one carbon by $^{13}C$- or $^{14}C$-enriched carbon, or the replacement of at least one nitrogen by $^{15}N$-enriched nitrogen are within the scope of this invention.

The compounds of formula (I) or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts, solvates or prodrugs.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value.

In the compounds of the present invention ⁻⁻⁻⁻ A represents =O or OH. In a particular embodiment, ⁻⁻⁻⁻ A is =O.

According to a particular embodiment, in the compounds of the present invention $R^1$ is hydrogen or a hydroxyl protecting group and $R^2$ is selected from

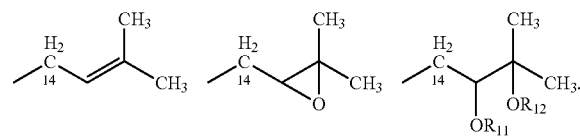

More particularly, $R^1$ is hydrogen or a hydroxyl protecting group and $R^2$ is

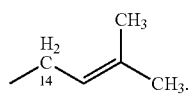

Even more particularly, $R^1$ is hydrogen or methyl and $R^2$ is

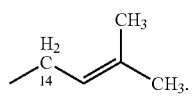

According to another particular embodiment, in the compounds of the present invention $R^1$ and $R^2$ together form a ring selected from

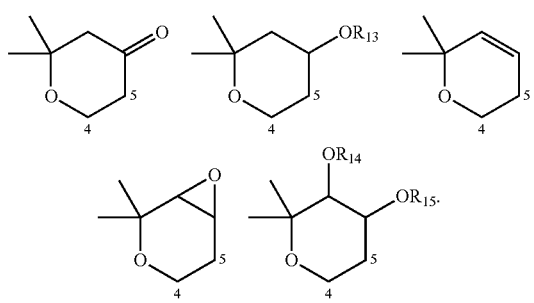

More particularly, $R^1$ and $R^2$ together form a ring selected from

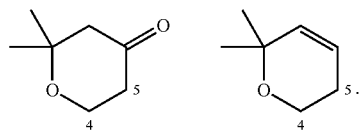

In the compounds of the present invention, $R^3$ is hydrogen or a hydroxyl protecting group. In a particular embodiment, $R^3$ is hydrogen.

In the compounds of the present invention, $R^5$ is hydrogen or halogen such as chloro. In a particular embodiment, $R^5$ is hydrogen or chloro.

According to a particular embodiment, in the compounds of the present invention $R^6$ is hydrogen and $R^7$ is CHO or $CH_2(OH)$. More particularly, $R^6$ is hydrogen and $R^7$ is CHO.

According to another particular embodiment, in the compounds of the present invention $R^6$ and $R^7$ together form a single bond.

In the compounds of the present invention, $R^8$ is hydrogen or a hydroxyl protecting group. In a particular embodiment, $R^8$ is hydrogen.

Representative hydroxyl protecting groups for $R^1$, $R^3$, $R^6$, $R^8$, $R^{11}$, $R^{12}$, $R^{13}$, $R^{14}$ and $R^{15}$ are:
  ethers of formula —R';
  esters of formula —C(=O)R'; and
  carbonates of formula —C(=O)OR';
  wherein R' can be independently selected from substituted or unsubstituted alkyl and substituted or unsubstituted aryl.

As the skilled person knows, hydroxyl protecting groups are commonly named considering the oxygen atom. Thus, terms such as "ether", "ester" and "carbonate" really refer herein to the chemical group formed with the oxygen atom i.e. —OR', —OC(=O)R' or —OC(=O)OR', respectively.

More particularly, hydroxy protecting groups include ethers such as methyl ether, tert-butyl ether, benzyl ether, p-methoxybenzyl ether, 3,4-dimethoxybenzyl ether, trityl ether, allyl ether, methoxym ethyl ether, 2-methoxyethoxymethyl ether, benzyloxymethyl ether, p-methoxybenzyloxymethyl ether, 2-(trimethylsilyl)ethoxymethyl, 1-methoxyethyl ether, 1-ethoxyethyl ether, 1-n-propoxyethyl ether, 1-isopropoxyethyl ether, 1-n-butoxyethyl ether, 1-isobutoxyethyl ether, 1-sec-butoxyethyl ether, 1-tert-butoxyethyl ether, 1-ethoxy-n-propyl ether, methoxypropyl ether, ethoxypropyl ether, 1-methoxy-1-methylethyl ether, 1-ethoxy-1-methylethyl ether; tetrahydropyranyl and related ethers; esters such as acetate, benzoate, pivaloate, methoxyacetate, chloroacetate, levulinate; carbonates such as benzyl carbonate, p-nitrobenzyl carbonate, tert-butyl carbonate, 2,2,2-trichloroethyl carbonate, 2-(trimethylsilyl)ethyl carbonate, allyl carbonate.

Particularly preferred compounds of the invention are the following:

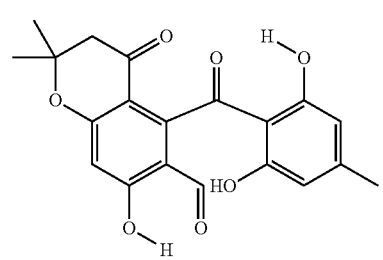

MDN-0089

-continued

MDN-0090
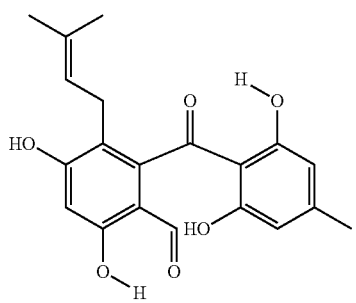

MDN-0091
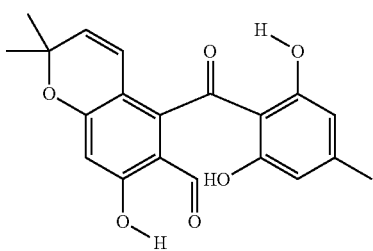

MDN-0092
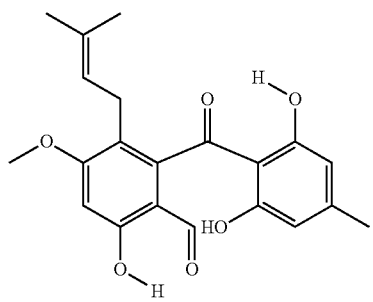

MDN-0093
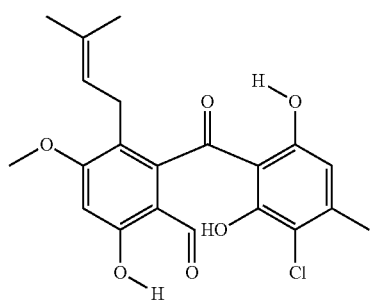

MDN-0094
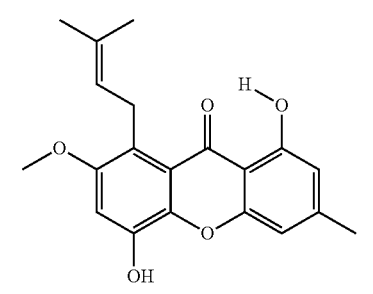

or pharmaceutically acceptable salts, stereoisomers or solvates thereof.

In additional preferred embodiments, the preferences described above for the different groups and substituents in the formulae above are combined. The present invention is also directed to such combinations.

Compounds MDN-0089 to MDN-0094 were isolated from a fungus identified as *Onychocola* sp. The fungus is deposited in the culture collection of Fundación MEDINA under the accession number CF-107644 and has been deposited under the Budapest treaty in the culture collection of the Centraalbureau voor Schimmelcultures Uppsalalaan 8, 3584 CT Utrecht, the Netherlands, with accession number CBS 139230.

One aspect of the present invention is said strain of *Onychocola* sp. deposited at the CBS with accession number CBS 139230 as well as a culture thereof including a biologically pure culture. A description of this microorganism is provided hereinafter in the experimental part.

Thus, the antitumoral compounds of the invention may be produced by cultivating the strain *Onychocola* CF-107644, CBS 139230, in a suitable nutrient medium, such as those described below, until a significant amount accumulates in the fermentation.

The strain is usually cultured in an aqueous nutrient medium containing sources of assimilable carbon and nitrogen. For example, the cultures may be grown under submerged aerobic conditions (e.g., shaking the culture, submerging the culture, etc.) or in solid state fermentations. The aqueous medium is preferably maintained at a pH of about 6-8, at the initiation and termination (harvest) of the fermentation process. The desired pH may be maintained by the use of a buffer, such as morpholinoethane-sulfonic acid (MES), morpholinopropane-sulfonic acid (MOPS), and the like, or by choosing nutrient materials that inherently possess buffering properties. Suitable sources of carbon in the nutrient medium include carbohydrates, such as glucose, xylose, galactose, glycerine, starch, sucrose, dextrin and the like. Other suitable carbon sources that may be used include maltose, rhamnose, raffinose, arabinose, mannose, sodium succinate and the like. Suitable sources of nitrogen are yeast extracts, meat extracts, peptone, gluten meal, cottonseed meal, soybean meal and other vegetable meals (partially or totally defatted), casein hydrolysates, soybean hydrolysates, yeast hydrolysates, corn steep liquor, dried yeast, wheat germ, feather meal, peanut powder, distiller's solubles and the like, as well as inorganic and organic nitrogen compounds, such as ammonium salts (including ammonium nitrate, ammonium sulfate, ammonium phosphate, etc.), urea, amino acids, and the like. The carbon and nitrogen sources, which may be advantageously employed in combination, do not need to be used in their pure forms; because less pure materials, which contain traces of growth factors, vitamins and significant quantities of mineral nutrients, are also suitable for use. In the case it would be necessary, mineral salts, such as sodium or calcium carbonate, sodium or potassium phosphate, sodium or potassium chloride, sodium or potassium iodide, magnesium salts, copper salts, cobalt salts, and the like, may be added to the medium. If necessary, especially when a culture medium foams excessively, one or more defoaming agent(s), such as liquid paraffin, fatty oils, plant oils, mineral oils or silicones, may be added. Submerged aerobic cultural conditions are typical methods of culturing cells for the production of cells in massive amounts. For small-scale production, a shaken or surface culture in a flask or bottle may be employed. When growth is carried out in large tanks, it may be preferable to use the vegetative forms of the organism for inoculation in the production tanks in order to avoid growth lag in the process of production. Accordingly, it may be desirable first to produce a vegetative inoculum of the organism by inoculating a relatively small quantity of culture medium with spores or mycelia of the organism produced in a "slant" or Petri dish and culturing said inoculated medium, also called the "seed medium," and then to transfer the cultured vegetative inoculum aseptically to large tanks. The fermentation medium, in which the inoculum is produced, is generally autoclaved to sterilize the medium prior to inoculation. The pH of the medium is generally adjusted to about 6-7 prior to the autoclaving step. Agitation and aeration of the culture mixture may be accomplished in a variety of ways. Agitation may be provided by a propeller or similar mechanical agitation equipment, by revolving or shaking the fermentor, by various pumping equipment, or by the passage of sterile air through the medium. The fermentation is usually conducted at a temperature between about 20° C. and 30° C., such as between about 22° C. and 25° C., for a period of about 7 to 21 days, and parameters may be varied according to fermentation conditions and scales. Preferred culturing/production media for carrying out the fermentation include the media as set forth in the examples. Culture media such as LSFM or BRFT are particularly preferred.

Separation and purification of compounds of the present invention from the crude active extract can be performed using the proper combination of conventional chromatographic techniques.

Additionally, compounds of the invention can be obtained by modifying those already obtained from the natural source or by further modifying those already modified by using a variety of chemical reactions, for instance by means of derivatization, protection/deprotection and isomerisation reactions. Thus, hydroxyl groups can be acylated by standard coupling or acylation procedures, for instance by using acetic acid, acetyl chloride or acetic anhydride in pyridine or the like. Formate groups can be obtained by heating hydroxyl precursors in formic acid. Carbamates can be obtained by heating hydroxyl precursors with isocyanates. Hydroxyl groups can be converted into halogen groups through intermediate sulfonates for iodide, bromide or chloride, or directly using a sulfur trifluoride for fluorides; or they can be reduced to hydrogen by reduction of intermediate sulfonates. Hydroxyl groups can also be converted into alkoxy groups by alkylation using an alkyl bromide, iodide or sulfonate, or into amino lower alkoxy groups by using, for instance, a protected 2-bromoethylamine. Amide groups can be alkylated or acylated by standard alkylation or acylation procedures, for instance by using, respectively, KH and methyl iodide or acetyl chloride in pyridine or the like. Ester groups can be hydrolized to carboxylic acids or reduced to aldehyde or to alcohol. Carboxylic acids can be coupled with amines to provide amides by standard coupling or acylation procedures. Carbonyl compounds can be reduced to alcohols by standard procedures. Double bonds can be epoxidized by known methods. When necessary, appropriate protecting groups can be used on the substituents to ensure that reactive groups are not affected. The procedures and reagents needed to prepare these derivatives are known to the skilled person and can be found in general textbooks such as March's Advanced Organic Chemistry 6th Edition 2007, Wiley Interscience. As the skilled person will appreciate, certain compounds of formula (I) may be useful as intermediate products in the preparation of other compounds of formula (I).

An important feature of the above described compounds is their bioactivity and in particular their activity as inhibitors of the Ras/Raf/MEK/ERK pathway and therefore their utility in cancer therapy. Thus, a further aspect of the present invention relates to a medicament or composition in different pharmaceutical forms comprising at least a compound of formula (I), optionally at least another anticancer drug and at least one pharmaceutically acceptable excipient for use in the treatment and/or prevention of cancer.

Examples of pharmaceutical compositions include any solid (tablets, pills, capsules, granules, etc.) semi-solid (creams, ointments, etc.) or liquid (solutions, suspensions or emulsions) composition for oral, topical or parenteral (such as intravenous) administration.

The respective medicament may—depending on its route of administration—also contain one or more excipients known to those skilled in the art. The medicament according to the present invention may be produced according to standard procedures known to those skilled in the art.

The term "excipient" refers to components of a drug compound other than the active ingredient (definition obtained from the European Medicines Agency—EMA). They preferably include a "carrier, adjuvant and/or vehicle". Carriers are forms to which substances are incorporated to improve the delivery and the effectiveness of drugs. Drug carriers are used in drug-delivery systems such as the controlled-release technology to prolong in vivo drug actions, decrease drug metabolism, and reduce drug toxicity. Carriers are also used in designs to increase the effectiveness of drug delivery to the target sites of pharmacological actions (U.S. National Library of Medicine. National Institutes of Health). Adjuvant is a substance added to a drug product formulation that affects the action of the active ingredient in a predictable way. Vehicle is an excipient or a substance, preferably without therapeutic action, used as a medium to give bulk for the administration of medicines (Stedman's Medical Spellchecker, @ 2006 Lippincott Williams & Wilkins). Such pharmaceutical carriers, adjuvants or vehicles can be sterile liquids, such as water and oils, including those of petroleum, animal, vegetable or synthetic origin, such as peanut oil, soybean oil, mineral oil, sesame oil and the like, excipients, disgregants, wetting agents or diluents. Suitable pharmaceutical carriers are described in "Remington's Pharmaceutical Sciences" by E. W. Martin. The selection of these excipients and the amounts to be used will depend on the form of application of the pharmaceutical composition.

As used herein, the terms "treat", "treating" and "treatment" include in general the eradication, removal, reversion, alleviation, modification, or control of cancer after its onset.

As used herein, the terms "prevention", "preventing", "preventive", "prevent" and "prophylaxis" refer to the capacity of a given substance, composition or medicament to avoid, minimize or difficult the onset or development of cancer before its onset.

The present invention also encompasses the combination of the compounds of formula (I) with other anticancer drug. A combination of at least a compound of formula (I) and at least another anticancer drug may be formulated for its simultaneous, separate or sequential administration. This has the implication that the combination of the two compounds may be administered:

as a combination that is being part of the same medicament formulation, the two compounds being then administered always simultaneously.

as a combination of two units, each with one of the substances giving rise to the possibility of simultaneous, sequential or separate administration.

In a particular embodiment, the compound of formula (I) is independently administered from the other anticancer drug (i.e in two units) but at the same time.

In another particular embodiment, the compound of formula (I) is administered first, and then the other anticancer drug is separately or sequentially administered.

In yet another particular embodiment, the other anticancer drug is administered first, and then the compound of formula (I) is administered, separately or sequentially, as defined.

Another aspect of the invention is a method of treatment of a patient, notably a human, suffering cancer, or likely to suffer cancer, which comprises administering to the patient in need of such a treatment or prophylaxis an effective amount of a compound of formula (I).

Examples of cancers on which the compounds of formula (I) of the invention may be used include, without limitation, pancreatic cancer.

By an "effective" amount or a "therapeutically effective amount" of a drug or pharmacologically active agent is meant a nontoxic but sufficient amount of the drug or agent to provide the desired effect. In the therapy of the present invention, an "effective amount" of the compound of formula (I) is the amount of that compound that is effective to provide the desired effect. The amount that is "effective" will vary from subject to subject, depending on the age and general condition of the individual, the particular active agent or agents, and the like. Thus, it is not always possible to specify an exact "effective amount". However, an appropriate "effective" amount in any individual case may be determined by one of ordinary skill in the art using routine experimentation.

The following examples are merely illustrative of certain embodiments of the invention and cannot be considered as restricting it in any way.

EXAMPLES

Example 1: Description of Fungal Strain

The producer fungus (CF-107644; CBS 139230) was isolated from a soil sample collected in Spain.

On 2% malt agar, the fungus presents golden colonies, moderately grown mycelia, cushion-shaped, yellow, with tan to reddish-brown reverse. Hyphae are hyaline, 1-2 μm wide, bearing lateral, tightly coiled fertile branches which disarticulate into arthroconidia; conidia alternate with empty cells. Conidia are cylindrical with truncate ends, pale yellowish, 3-6.5×2.5-4.5 μm.

To estimate the phylogenetic position of strain CF-107644, genomic DNA was extracted from mycelia grown on malt-yeast extract agar. The rDNA region containing the partial sequence of 28S rDNA containing D1 D2 variable domains was amplified with primers NL1 and NL4 (O'Donnell K, 1993. Fusarium and its near relatives. In: Reynolds D R, Tailor J W (eds). The fungal holomorph: mitotic, meiotic and pleomorphic speciation in fungal systematic, CAB international, Wallingford, UK, pp. 225-233) and a DNA sequence was generated. About 0.1 μg/mL of the double-stranded amplification products were sequenced using the ABI PRISM Dye Terminator Cycle Sequencing Ready Reaction Kit (Perkin Elmer, Norwalk Conn.;) following the procedures recommended by the manufacturer. Purified PCR products were directly sequenced using the same primer pairs as in the PCR reactions. Partial sequences obtained in sequencing reactions were assembled with Genestudio 2.1.1.5. (Genestudio, Inc., Suwanee, Ga., USA). Database matching with the 28S rDNA sequence (www.fungalbar.org), yielded a very high sequence similarity (99%) to the strain of *Arachnomyces nitidus* IFO 32048, thus indicating that strain CF-107644 was genetically similar to *A. nitidus*, and probably congener. High similar scores (99%) to other authentic fungus strains *Arachnomyces nitidus* NBRC 32048 indicated that CF-107644 could be classified as *Onychocola* sp. anamorphous to *Arachnomyces* sp. (*Ascomycota, Pezizomycotina, Eurotiomycetes, Eurotiomycetidae, Arachnomycetales, Arachnomycetaceae*).

Example 2: Fermentation in Submerged Liquid Media

The most potent activity from extracts of a medium designated as LSFM (Glycerol 18.7 g, glucose 40 g, $NH_4SO_4$ 2 g, Sigma yeast autolysate 5 g, soybean meal 5 g, tomato paste 5 g, Na citrate 2 g, distilled $H_2O$ 1000 mL) was selected for further study. The initial sample for characterization of MAPK pathway inhibitor activity was prepared by cutting five mycelial discs from each 60-mm plate and crushing them in the bottom of tubes (25×150 mm) containing 12 mL of Sabouraud maltose broth supplemented with yeast extract and dilute agar (SMYA) (Difco neopeptone 10 g, maltose 40 g, Difco yeast extract 10 g, agar 4 g, distilled $H_2O$ 1000 mL) and two cover glasses (22×22 mm). Tubes were agitated on an orbital shaker (220 rpm, 5 cm throw), to produce homogenous hyphal suspensions. After growing the inoculum stage for 7 days, a 0.3 mL aliquot was used to inoculate 10 mL of LSFM medium in 2×10-mL EPA vials. The tubes were incubated in aerated agitated fermentation (220 rpm) for 21 days at 22° C. Mycelium and broth from these tubes were extracted with acetone, and after removing the acetone by evaporation, the aqueous residue was used to detect a series of active molecules. To further characterize the molecules responsible for the activity, 1-L fermentation was prepared. Ten mycelial discs were used to inoculate 50 mL of SMYA. After 7 days, 3-mL aliquots of this culture were used to inoculate LSFM medium (10×100 mL medium in 500-mL Erlenmeyer flasks). The flasks were incubated in an aerated agitated fermentation (220 rpm, 5 cm throw) at 22° C., 70% relative humidity for 21 days.

Example 3: Fermentation in Solid Media

Cultivation of the said fungus in BRFT [Brown rice 20 g, base liquid 40 mL (yeast extract 1 g, sodium tartate 0.5 g, $KH_2PO_4$ 0.5 g, distilled water 1000 mL) per 500-mL Erlenmeyer flask] solid medium was also conducted, yielding a broader spectrum of chemical derivatives of compound MDN-0090.

To further characterize said molecules in this example, a 400 mL fermentation was prepared. Ten mycelial discs were used to inoculate a culture of 50 mL of SMYA. After 7 days, 3-mL aliquots of this culture were used to inoculate BRFT medium (10 Erlenmeyer flasks). The flasks were incubated in static condition at 22° C., 70% relative humidity for 21 days.

Example 4: Isolation and Structural Identification of MDN-0089 to MDN-0094

The fermentation broth (1 L in flasks, BRFT medium) was extracted with acetone (1 L) under continuous shaking at 220 rpm for 2.5 h. The mycelium was separated by centrifugation and the supernatant (2 L) was concentrated to 1 L under a nitrogen stream removing most of the acetone. The remaining 1 L solution, after paper filtration, was loaded with continuous 1:1 water dilution onto a column packed with SP-207SS reversed phase resin (brominated styrenic polymer, 65 g) previously equilibrated with water. The column was further washed with water (1 L) and afterwards eluted at 18 mL/min using a stepped gradient from 20% to 100% acetone in water for 20 min with a final 100% acetone wash step of 12 min collecting 15 fractions of 18 mL. Bioassay of the fractions obtained located the compounds of interest in the 80-100% acetone-water fractions (collected in three fractions).

These fractions were further purified by reversed phase preparative HPLC (Agilent Zorbax SB-C8, 21.2×250 mm, 7 μm; 20 mL/min, UV detection at 210 nm and 280 nm) with a linear gradient of $CH_3CN$ in water (0.1% TFA) from 45% to 80% $CH_3CN$-TFA over 35 min where fractions containing compound MDN-0089 eluted at 10.0 min, MDN-0090 eluted at 11.1 min, MDN-0091 at 13.5 min, MDN-0092 at 16.0 min, MDN-0093 at 18.4 min and MDN-0094 at 22.0 min.

Fractions containing MDN-0089 and MDN-0090 were further purified by reversed phase semipreparative HPLC (Agilent Zorbax RX-C8, 9.4×250 mm, 5 μm; 3.6 mL/min UV detection at 210 nm and 280 nm) with a linear gradient of $CH_3CN$ in water from 50% to 65% over 34 min where fractions containing compound MDN-0089 (5.8 mg) eluted at 11.25 min and MDN-0090 (6.6 mg) eluted at 13.0 min.

Fractions containing MDN-0091 and MDN-0092 were further purified by reversed phase semipreparative HPLC (Agilent Zorbax RX-C8, 9.4×250 mm, 5 μm; 3.6 mL/min UV detection at 210 nm and 280 nm) with a linear gradient of $CH_3CN$ in water from 55% to 65% over 34 min where fractions containing compounds MDN-0091 (4.8 mg) and MDN-0092 (6.0 mg) eluted at 12.5 min and 15.5 min, respectively.

Fractions containing MDN-0093 were further purified by reversed phase semipreparative HPLC (Agilent Zorbax RX-C8, 9.4×250 mm, 5 μm; 3.6 mL/min UV detection at 210 nm and 280 nm) with a linear gradient of $CH_3CN$ in water from 58% to 70% over 34 min where compound MDN-0093 (4.0 mg) eluted at 15.25 min.

Fractions containing MDN-0094 were further purified by reversed phase semipreparative HPLC (Agilent Zorbax RX-C8, 9.4×250 mm, 5 μm; 3.6 mL/min UV detection at 210 nm and 280 nm) with a linear gradient of $CH_3CN$ in water from 60% to 68% over 34 min where compound MDN-0094 (7.2 mg) eluted at 18.0 min. MDN-0089: yellow solid; UV (DAD) $\lambda_{max}$ 264, 288 & 332(sh) nm; IR (ATR) γ $cm^{-1}$: 3166, 2978, 1690, 1636, 1573, 1468, 1373, 1342, 1263, 1201, 1161, 1078, 826, 771. HRMS m/z 371.1128 [M+H]$^+$ (calc. for $C_{20}H_{19}O_7^+$, 371.1125, Δ 0.7 ppm); 388.1390 [M+NH$_4$]$^+$ (calc. for $C_{20}H_{22}NO_7^+$, 388.1391, Δ −0.2 ppm); $^1$H and $^{13}$C NMR data see Table 1:

TABLE 1

NMR Spectroscopic Data (500 MHz, CDCl$_3$, 24° C.) for MDN-0089.

| no | $\delta_C$, type | $\delta_H$, mult. (J in Hz) | NOESY | HMBC (H to C) |
|---|---|---|---|---|
| 1 | 112.9, C | | | |
| 2 | 168.2, C | | | |
| 3 | 105, CH | 6.43, s | | 1, 2, 4, 5 |
| 4 | 166.0, C | | | |
| 5 | 111.4, C | | | |
| 6 | 150.6, C | | | |
| 7 | 198.1, C | | | |
| 8 | 109.5, C | | | |
| 9 | 163.9, C | | | |
| 10 | 111.2, CH | 6.45, bs | | 12, 21 |
| 11 | 149.9, C | | | |
| 12 | 107.4, CH | 5.93, bs | | 10, 21 |
| 13 | 150.4, C | | | |
| 14 | 190.1, C | | | |
| 15 | 48.6, CH$_2$ | 2.69, d (16.7) | | 14, 16, 17, 18 |
| | | 2.61, d (16.7) | | 14, 16, 17, 18 |
| 16 | 80.9, C | | | |

TABLE 1-continued

NMR Spectroscopic Data (500 MHz, CDCl$_3$, 24° C.) for MDN-0089.

| no | $\delta_C$, type | $\delta_H$, mult. (J in Hz) | NOESY | HMBC (H to C) |
|---|---|---|---|---|
| 17 | 27.0, CH$_3$ | 1.49, s | 15 | 15, 16, 18 |
| 18 | 26.7, CH$_3$ | 1.45, s | 15 | 15, 16, 17 |
| 20 | 193.4, CH | 9.65, s | | 1, 2, 3 |
| 21 | 22.2, CH$_3$ | 2.23, s | 10, 12 | 10, 11, 12 |
| 22 | | 12.46, bs | | 8, 9 |
| 23 | | 12.10, s | | 1, 2, 3 |

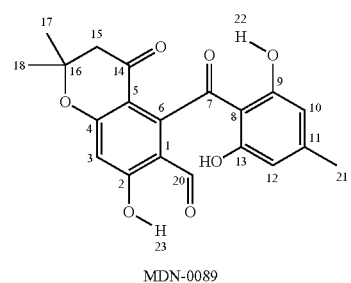

MDN-0089

MDN-0090: yellow solid; UV (DAD) $\lambda_{max}$ 288, 329(sh) nm; IR (ATR) γ $cm^{-1}$: 3294, 2979, 2914, 2858, 1630, 1575, 1444, 1376, 1297, 1244, 1208, 1173, 1079, 829, 732. HRMS m/z 357.1330 [M+H]$^+$ (calc. for $C_{200}H_{21}O_6^+$, 357.1333, Δ −0.7 ppm); 379.1147 [M+Na]$^+$ (calc. for $C_{20}H_{20}O_6Na^+$, 379.1152, Δ −1.3 ppm); 339.1223 [M+H—H$_2$O]$^+$ (calc. for $C_{20}H_{19}O_5^+$, 339.1227, Δ −1.2 ppm); $^1$H and $^{13}$C NMR data see Table 2:

TABLE 2

NMR Spectroscopic Data (500 MHz, CDCl$_3$, 24° C.) for MDN-0090.

| no | $\delta_C$, type | $\delta_H$, mult. (J in Hz) | COSY | NOESY | HMBC (H to C) |
|---|---|---|---|---|---|
| 1 | 111.8, C | | | | |
| 2 | 163.5, C | | | | |
| 3 | 104.0, CH | 6.35, s | | | 1, 2, 4, 5 |
| 4 | 163.0, C | | | | |
| 5 | 116.3, C | | | | |
| 6 | 146.9, C | | | | |
| 7 | 198.9, C | | | | |
| 8 | 109.8, C | | | | |
| 9 | 163.4, C | | | | |
| 10 | 111.0, CH | 6.43, bs | | | 8, 12, 21 |
| 11 | 151.7, C | | | | |
| 12 | 108.3, CH | 6.04, bs | | | 8, 10, 21 |
| 13 | 158.2, C | | | | |
| 14 | 26.0, CH$_2$ | 3.17, d (6.8) | 15, 17, 18 | 15, 18 | 4, 5, 6, 15, 16 |
| 15 | 120.6, CH | 5.08, dd (6.5, 6.7) | 14, 17, 18 | 14, 17 | 5, 17, 18 |
| 16 | 135.7, C | | | | |
| 17 | 17.8, CH$_3$ | 1.58, s | | 14 | 15, 16, 17 |
| 18 | 25.8, CH$_3$ | 1.61, s | | 15 | 15, 16, 18 |
| 20 | 192.6, CH | 9.55, s | | | 1, 2, 3 |
| 21 | 22.4, CH$_3$ | 2.26, s | | | 10, 11, 12 |
| 22 | | 12.76, s | | | 8, 9, 10 |
| 23 | | 11.93, bs | | | |

TABLE 2-continued

NMR Spectroscopic Data (500 MHz, CDCl₃, 24° C.) for MDN-0090.

| no | $\delta_C$, type | $\delta_H$, mult. (J in Hz) | COSY | NOESY | HMBC (H to C) |
|----|------|------|------|------|------|

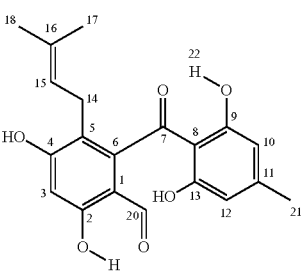

MDN-0090

MDN-0091: yellow solid; UV (DAD) $\lambda_{max}$ 264, 288, 360 (sh) nm; IR (ATR) γ cm⁻¹: 3313, 2977, 2928, 2865, 1635, 1583, 1455, 1374, 1305, 1258, 1212, 1155, 1112, 829. HRMS m/z 355.1179 [M+H]⁺ (calc. for $C_{20}H_{19}O_6^+$, 355.1176, Δ 0.8 ppm); 377.0994 [M+Na]⁺ (calc. for $C_{20}H_{18}O_6Na^+$, Δ –377.0996, Δ –0.5 ppm); ¹H and ¹³C NMR data see Table 3:

TABLE 3

NMR Spectroscopic Data (500 MHz, CDCl₃, 4° C.) for MDN-0091.

| no | $\delta_C$, type | $\delta_H$, mult. (J in Hz) | COSY | NOESY | HMBC (H to C) |
|----|------|------|------|------|------|
| 1 | 111.6, C | | | | |
| 2 | 164.8, C | | | | |
| 3 | 104.7, CH | 6.35, s | | 17, 18 | 1, 2, 4, 5 |
| 4 | 161.2, C | | | | |
| 5 | 110.7, C | | | | |
| 6 | 142.9, C | | | | |
| 7 | 198.3, C | | | | |
| 8 | 109.5, C | | | | |
| 9 | 164.3, C | | | | |
| 10 | 111.0, CH | 6.43, bs | | | 8, 12, 21 |
| 11 | 151.8, C | | | | |
| 12 | 108.2, CH | 6.03, bs | | | 8, 10, 21 |
| 13 | 158.1, C | | | | |
| 14 | 117.4, CH | 6.06, d (10.8) | 15 | 15, 17, 18 | 4, 5, 6, 16 |
| 15 | 130.6, CH | 5.59, d (10.1) | 14 | 14, 17, 18 | 5, 16, 17, 18 |
| 16 | 78.4, C | | | | |
| 17 | 28.7, CH₃ | 1.43, s | | 3, 14, 15 | 15, 16, 18 |
| 18 | 28.5, CH₃ | 1.43, s | | 3, 14, 15 | 15, 16, 17 |
| 20 | 192.3, CH | 9.54, s | | | 1, 2, 3 |
| 21 | 22.5, CH₃ | 2.26, s | | | 10, 11, 12 |
| 22 | | 12.78, bs | | | 8, 9, 10 |
| 23 | | 11.98, s | | | 1, 2, 3, 4 |
| 24 | | 5.80, bs | | | |

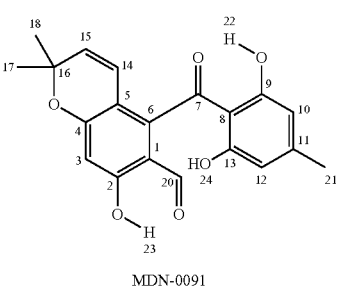

MDN-0091

MDN-0092: yellow solid; UV (DAD) $\lambda_{max}$ 232, 288, 332 (sh) nm; IR (ATR) γ cm⁻¹: 3289, 2967, 2918, 2855, 1636, 1581, 1439, 1374, 1305, 1250, 1209, 1166, 1082, 981. HRMS m/z 371.1496 [M+H]⁺ (calc. for $C_{21}H_{23}O_6^+$, 371.1489, Δ 1.9 ppm); 353.1390 [M+H—H₂O]⁺ (calc. for $C_{21}H_{21}O_5^+$, 353.1389, Δ 0.3 ppm); ¹H and ¹³C NMR data see Table 4:

TABLE 4

NMR Spectroscopic Data (500 MHz, CDCl₃, 24° C.) for MDN-0092.

| no | $\delta_C$, type | $\delta_H$, mult. (J in Hz) | COSY | NOESY | HMBC (H to C) |
|----|------|------|------|------|------|
| 1 | 111.3, C | | | | |
| 2 | 164.2, C | | | | |
| 3 | 99.2, CH | 6.44, s | | 19 | 1, 2, 4, 5 |
| 4 | 165.0, C | | | | |
| 5 | 118.6, C | | | | |
| 6 | 146.1, C | | | | |
| 7 | 198.9, C | | | | |
| 8 | 110.0, C | | | | |
| 9 | 164.4, C | | | | |
| 10 | 110.4, CH | 6.39, s | | 21 | 8, 12, 21 |
| 11 | 151.2, C | | | | |
| 12 | 108.3, CH | 6.06, s | | 21 | 8, 10, 21 |
| 13 | 158.9, C | | | | |
| 14 | 25.4, CH₂ | 3.18, dd (7.9, 14.9) 3.11, dd (6.2, 15.2) | 15 | 15, 17 | 4, 5, 6, 15, 16 |
| 15 | 121.3, CH | 4.98, dd (6.7) | 14 | 14, 18 | 14, 17, 18 |
| 16 | 132.7, C | | | | |
| 17 | 17.6, CH₃ | 1.45, s | | 14 | 15, 16, 18 |
| 18 | 25.7, CH₃ | 1.52, s | | 15 | 15, 16, 17 |
| 19 | 56.3, CH₃ | 3.89, s | | | 4 |
| 20 | 192.6, CH | 9.59, s | | | 1, 2, 3 |
| 21 | 22.4, CH₃ | 2.24, s | | | 10, 11, 12 |
| 22 | | 12.79, s | | | 8, 9, 10 |
| 23 | | 12.06, s | | | 1, 2, 3 |

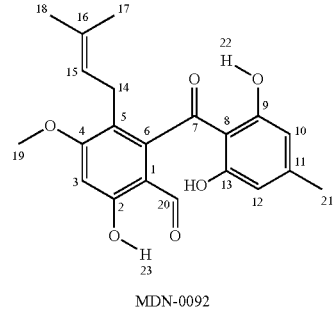

MDN-0092

MDN-0093: yellow solid; UV (DAD) $\lambda_{max}$ 286, 328(sh) nm; IR (ATR) γ cm⁻¹: 3366, 2965, 2924, 2856, 1632, 1440, 1375, 1323, 1301, 1263, 1237, 1205, 1165, 983, 837. HRMS m/z 405.1099 [M+H]⁺ (calc. for $C_{21}H_{23}O_6^+$, 405.1099, Δ 0 ppm); 387.0994 [M+H—H₂O]⁺ (calc. for $C_{21}H_{21}O_5^+$, 389.0999, Δ –1.3 ppm); ¹H and ¹³C NMR data see Table 5:

TABLE 5

NMR Spectroscopic Data (500 MHz, CDCl₃, 24° C.) for MDN-0093.

| no | $\delta_C$, type | $\delta_H$, mult. (J in Hz) | COSY | NOESY | HMBC (H to C) |
|----|------|------|------|------|------|
| 1 | 111.5, C | | | | |
| 2 | 164.1, C | | | | |
| 3 | 99.2, CH | 6.45, s | | 19 | 1, 2, 4, 5 |
| 4 | 164.8, C | | | | |
| 5 | 118.1, C | | | | |
| 6 | 146.3, C | | | | |
| 7 | 199.9, C | | | | |
| 8 | 110.2, C | | | | |
| 9 | 162.3, C | | | | |
| 10 | 112.0, CH | 6.56, s | | 21 | 8, 9, 12, 21 |
| 11 | 147.2, C | | | | |

TABLE 5-continued

NMR Spectroscopic Data (500 MHz, CDCl₃, 24° C.) for MDN-0093.

| no | δ_C, type | δ_H, mult. (J in Hz) | COSY | NOESY | HMBC (H to C) |
|---|---|---|---|---|---|
| 12 | 111.3, C | | | | |
| 13 | 152.9, C | | | | |
| 14 | 25.5, CH₂ | 3.10, d (6.4) | 15 | | 4, 5, 6, 15, 16 |
| 15 | 121.5, CH | 4.94, dd (6.9) | 14 | | 5, 17, 18 |
| 16 | 132.3, C | | | | |
| 17 | 17.5, CH₃ | 1.39, s | | 14 | 15, 16, 18 |
| 18 | 25.7, CH₃ | 1.48, s | | 15 | 15, 16, 17 |
| 19 | 56.3, CH₃ | 3.90, s | | | 3, 4 |
| 20 | 192.2, CH | 9.56, s | | | 1, 2, 3 |
| 21 | 21.4, CH₃ | 2.37, s | | | 10, 11, 12 |
| 22 | | 12.70, s | | | 8, 9, 10 |
| 23 | | 12.01, s | | | 1, 2, 3 |
| 24 | | 6.01, bs | | | |

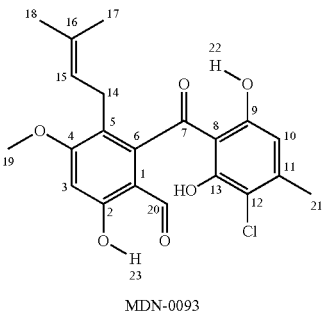

MDN-0093

MDN-0094: yellow solid; UV (DAD) λ_max 236, 266, 300, 324, 396 (sh) nm; IR (ATR) γ cm⁻¹: 3309, 2956, 2917, 2853, 1656, 1590, 1573, 1490, 1458, 1426, 1362, 1320, 1271, 1213, 1100, 978, 827. HRMS m/z 341.1385 [M+H]⁺ (calc. for $C_{20}H_{21}O_5^+$, 341.1384, Δ 0.3 ppm); 703.2513 [2M+Na]⁺ (calc. for $C_{40}H_{40}O_{10}Na^+$, 703.2514, Δ −0.1 ppm); ¹H and ¹³C NMR data see Table 6:

TABLE 6

NMR Spectroscopic Data (500 MHz, CDCl₃, 24° C.) for MDN-0094.

| no | δ_C, type | δ_H, mult. (J in Hz) | COSY | NOESY | HMBC (H to C) |
|---|---|---|---|---|---|
| 1 | 139.7, C | | | | |
| 2 | 143.2, C | | | | |
| 3 | 105.8, CH | 7.01, s | | 19 | 1, 2, 4, 5 |
| 4 | 153.6, C | | | | |
| 5 | 122.8, C | | | | |
| 6 | 119.1, C | | | | |
| 7 | 184.1, C | | | | |
| 8 | 107.5, C | | | | |
| 9 | 162.2, C | | | | |
| 10 | 111.6, CH | 6.59, s | | 21 | 8, 9, 12, 21 |
| 11 | 148.5, C | | | | |
| 12 | 106.5, C | 6.67, s | | 21 | 8, 10, 13, 21 |
| 13 | 154.8, C | | | | |
| 14 | 24.9, CH₂ | 4.04, d (6.7) | 15, 17, 18 | 15, 17 | 4, 5, 6, 15, 16 |
| 15 | 123.3, CH | 5.21, dd (6.8) | 14, 17, 18 | 14, 18 | 17, 18 |
| 16 | 131.9, C | | | | |
| 17 | 18.2, CH₃ | 1.84, s | | 14 | 15, 16, 18 |
| 18 | 26.1, CH₃ | 1.68, s | | 15 | 15, 16, 17 |
| 19 | 56.7, CH₃ | 3.85, s | | | 4 |
| 21 | 22.6, CH₃ | 2.41, s | | 10, 12 | 10, 11, 12 |
| 22 | | 12.93, s | | | 8, 9, 10 |
| 23 | | 5.79 | | | |

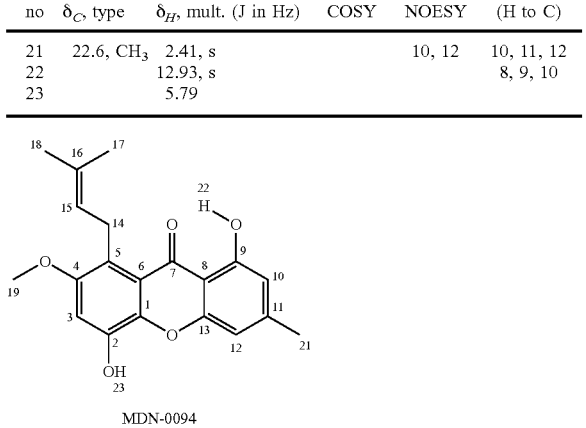

MDN-0094

Example 5: Scale Up of MDN-0090 Isolation

The fermentation broth (4.5 L in flasks, LSFM medium) was filtrated, and the cells were triturated and extracted with methyl ethyl ketone (6×1 L). The liquid supernatant was also extracted with the same organic solvent (2×3 L). The combined organic phases were evaporated to dryness to afford 17.7 g of a crude extract that was subjected to reversed phase silica gel (RP18) chromatography (70 g C18, 40-60 μm). The column was washed with 30% of CH₃CN in water for 7 min and eluted at 18 mL/min using a linear gradient from 30% to 100% CH₃CN in water for 43 min with a final 100% CH₃CN wash step of 10 min collecting 57 fractions of 18 mL. Compound MDN-0090 was detected to elute in the 70-80% CH₃CN fractions by HPLC-MS.

These fractions were further purified by reversed phase semi-preparative HPLC (x-Bridge C18, 10×150 mm, 5 μm; 3.6 mL/min, UV detection at 210 nm and 280 nm) with a linear gradient of CH₃CN in water from 45% to 55% over 35 min where compound MDN-0090 (675 mg) eluted at 12.5 min.

Example 6: Assessment of the Antitumoral Activity of Compounds MDN-0089, MDN-0090, MDN-0091, MDN-0092, MDN-0093 and MDN-0094

The activity of the compounds was detected using tumoral pancreatic cell lines (MiaPaca-2 and BxPC3). For this purpose MTT test was used. Cells were seeded at 10⁶ cells/well, and treated with the compound during 72 hours.

TABLE 7

Results of MTT assay in MiaPaca_2 and BxPC3 cell lines

| Compound | ED50 (μM) | |
|---|---|---|
| | MiaPaca_2 | BxPC3 |
| MDN-0089 | 20.34 | 7.63 |
| MDN-0090 | 8.84 | 4.67 |
| MDN-0091 | >50 | >50 |
| MDN-0092 | 7.18 | 9.14 |
| MDN-0093 | 6.47 | 8.7 |
| MDN-0094 | >50 | >50 |

The growth inhibitory effect on tumoral pancreatic cell lines for MDN-0090 can also be observed in FIG. 1.

Example 7: Assessment of the Cytotoxicity and Apoptosis Activities of Compounds MDN-0089, MDN-0090, MDN-0092 and MDN-0093

The MiaPaca 2 cell line was used for further evaluation of the MDN-0089, MDN-0090, MDN-0092 and MDN-0093 activity. The ApoTox-Glo™ Triplex Assay was used to evaluate three parameters (viability, citotoxicity and apoptosis).

Viability: The live-cell protease activity is restricted to intact viable cells and is measured using a fluorogenic, cell-permeant, peptide substrate (glycylphenylalanyl-aminofluorocoumarin; GF-AFC). The substrate enters intact cells where it is cleaved by the live-cell protease activity to generate a fluorescent signal proportional to the number of living cells Cytotoxicity: Fluorogenic cell-impermeant peptide substrate (bis-alanylalanyl-phenylalanyl-rhodamine 110; bis-AAF-R110) is used to measure dead-cell protease activity, which is released from cells that have lost membrane integrity. Because bis-AAF-R110 is not cell-permeant, essentially no signal from this substrate is generated by intact, viable cells Apoptosis: The assay uses the Caspase-Glo® Assay Technology by providing a luminogenic caspase-3/7 substrate, which contains the tetrapeptide sequence DEVD, in a reagent optimized for caspase activity, luciferase activity and cell lysis.

TABLE 8

Results of MDN-0089, MDN-0090, MDN-0092 and MDN-0093 on MiaPaca_2 at 72 hours of treatment in ApoTox-Glo ™ Triplex Assay.

| Compound | ED50 ($\mu$M) | | |
|---|---|---|---|
| | Apoptosis (Caspase3_7) | Viability | Citotoxicity |
| MDN-0089 | 29.66 | >50 | >50 |
| MDN-0090 | 24.92 | 17.31 | >50 |
| MDN-0092 | >50 | >50 | >50 |
| MDN-0093 | 18.35 | 14.45 | >50 |

Example 8: Assessment of the Cell Cycle Inhibition Activity of Compounds MDN-0089, MDN-0090, MDN-0092 AND MDN-0093

To evaluate the potency of the MDN-0089, MDN-0090, MDN-0092 and MDN-0093, dye CFSE and High content screening (HCS) equipment were used. MiaPaca_2 cell line was used. Cells were seeded in 96 wells plates at 10.000 cells/well. Medium was removed and compounds and standards were added in fresh medium at different concentrations, (1 $\mu$L of compound/200 $\mu$L fresh medium). The DMSO concentration was 0.5% in all wells. After 72 hours of incubation (37° C., 5% $CO_2$), plates were read in HCS equipment.

TABLE 9

Results of MDN-0089, MDN-0090, MDN-0092 and MDN-0093 on MiaPaca_2 at 72 hours of treatment in CFSE assay.

| Compound ID | ED50 ($\mu$M) |
|---|---|
| MDN-0089 | 3.33 |
| MDN-0090 | 5.27 |
| MDN-0092 | 22.88 |
| MDN-0093 | <3.15 |

Example 9: Assessment of Ras/Raf/MEK/ERK Pathway Inhibitor of Compounds MDN-0089, MDN-0090, MDN-0092 AND MDN-0093

Western blot technique was used, using an Odissey Licor equipment to read the membranes. pERK1_2 antibody was used as first antibody and as second antibody we used anti-mouse antibodies. Then, the membranes were quantified using $\beta$-actin. Results are shown in table 10.

TABLE 10

Results of WB pERK1_2. Quantification of the fluorescence pERK1/2 in relation of amount of protein measured with $\beta$-actine (Fluorescence pERK1/2/fluorescence $\beta$-actine)

| | pERK1_2 |
|---|---|
| Untreated | 0.38 |
| STAUROSPORINE | 0.12 |
| MDN-0089 | 0.22 |
| MDN-0090 | 0.18 |
| MDN-0092 | 0.29 |
| MDN-0093 | 0.12 |

As shown in table 10, all of the compounds decreased the amount of pERK1_2 after 24 hours of treatment.

Figure 2:
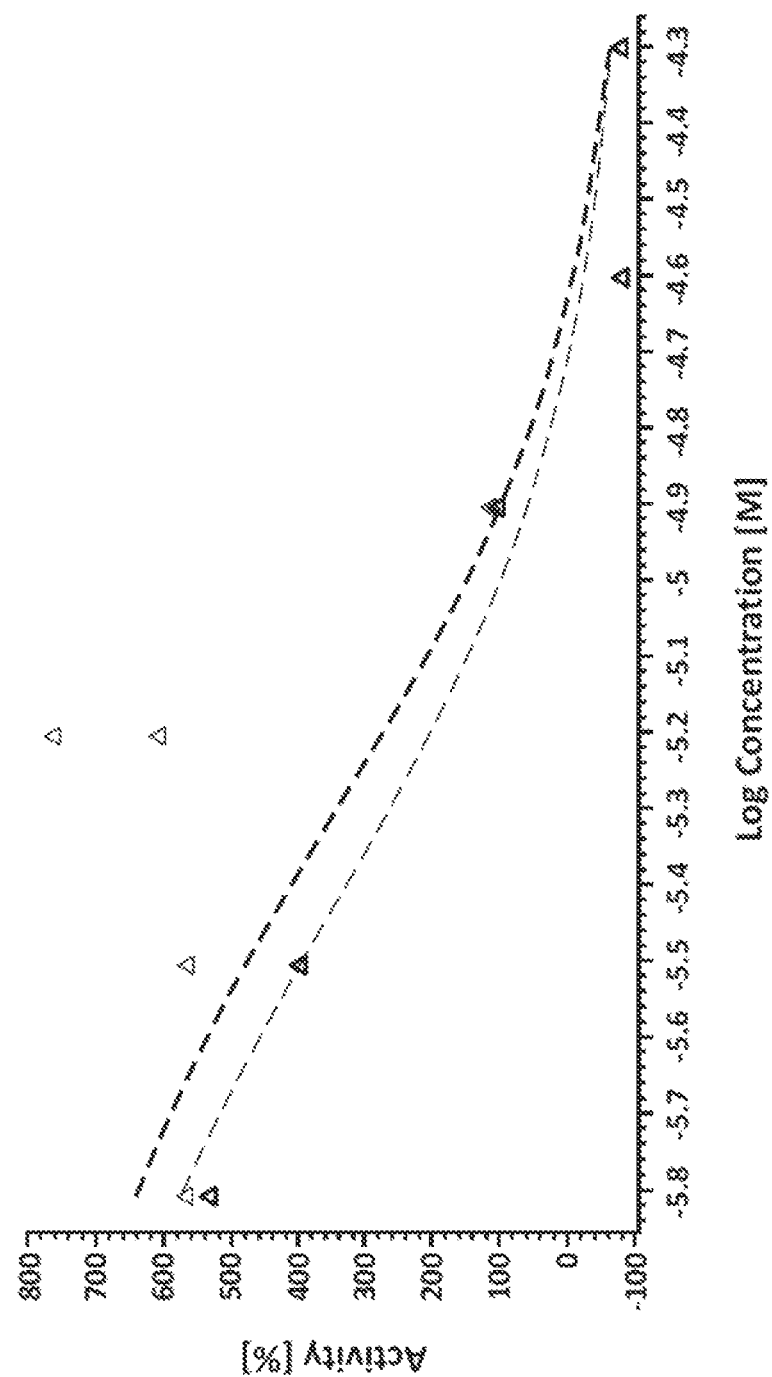
FIG. 2. Results of Alphascreen Surefire PERK assay. See example 9.

This effect was checked for MDN-0090 with a p-ERK kit (Perkin Elmer). Cells were seeded into 96 wells/plate at 75000 cells/well. 24 hours later the medium was removed and the compound was added with fresh medium. After 24 hours of treatment, cells were lysed. 15 $\mu$L of the lysate and 15 $\mu$L of reagents were added. After 2 hours of incubation, plate was read using an EnVision equipment to read AlphaScreen assay (AlphaScreen signal (Luminiscent/fluorescent). See table 11 and FIG. 2.

TABLE 11

| AlphaScreen results | | |
|---|---|---|
| Compound ID | Inflexion point ($\mu$M) | |
| MDN-0090 | 9.02 | 6.12 |

Example 10: Assessment of Cytotoxicity

MDN-0089, MDN-0090, and MDN-0092 displayed medium activity effect at 72 hours on HepG2. MDN-0093 displayed high activity effect at 72 hours on HepG2.

TABLE 12

Cytoxicity results

| Compound ID | $IC_{50}$ ($\mu$M) |
|---|---|
| MDN-0089 | 13.6 |
| MDN-0090 | 19.7 |

TABLE 12-continued

| Cytoxicity results | |
|---|---|
| Compound ID | IC$_{50}$ (µM) |
| MDN-0092 | 20.4 |
| MDN-0093 | 8.9 |

Example 11: Assessment of The Antitumoral Activity of Compound MDN-0090 Over Pancreatic Cancer Stem Cells Two established cell lines derived from two different pancreatic adenocarcinomas: BxPC3 (reference ATCC® CRL-1687), mutated for CDKN2A, MAP2K4, SMAD4 and TP53; and MIA-PaCa-2 (reference ATCC® CRL-1420), mutated for k-RAS were used. These cells lines were maintained with Dulbecco's-Modified Eagle's Medium (DMEM) (Sigma-Aldrich, St. Louis, Mo., USA) supplemented with 10% fetal bovine serum (FBS) (Gibco, Carlsbad, Calif., USA) and 1% penicillin/streptomycin (P/S) (Sigma-Aldrich) in a 75 cm$^2$ culture flask (B D Falcon, Franklin Lakes, N.J.) unless otherwise indicated. All cells were grown at 37° C. with 5% CO$_2$ in a humidified incubator (Steri-Cult CO$_2$ Incubator, Thermo Electron Corporation, Waltham, Mass., USA). Media were changed every 48-72 hours and cultured cells with a maximum of 80% confluence were passed.

Isolation and Enrichment of CSCs Subpopulations

For the isolation of CSCs subpopulation we used the methodology described in WO 2016/020572.

Characterization of Cancer Stem Cells

Aldefluor Assay

Aldehyde dehydrogenase (ALDH) enzyme activity in viable cells was determined by Aldefluor® kit assay (Stem Cell Technologies, Grenoble, France) according to the manufacturer's instructions. Aldefluor is supplied in the form of Bodipy™-aminoacetaldehyde-diethyl acetate (BAAA-DA) which by itself is not a substrate of ALDH. BAAA-DA was dissolved in DMSO and exposed to hydrochloric acid to convert it into Bodipy™-aminoacetaldehyde (BAAA) which is an uncharged fluorescent substrate for ALDH that can diffuse freely across the plasma membrane of intact viable cells. In the presence of ALDH, BAAA is converted into Bodipy™-aminoacetate (BAA), which is retained inside the cell. To perform the assay, 1×10$^6$ cells were resuspended in 1 mL Aldefluor® assay buffer that contains a transport inhibitor, which prevents efflux of the BAA from the cells. Then, 5 µL of BAAA was added to the cell suspension, 500 µL were transferred into another tube and 5 µL of the diethylamino-benzaldehyde (DEAB)-ALDH inhibitor was added. Both tubes were incubated for 30 minutes at 37° C. in the dark. Then, cells were spin down at 1500 rpm 5 minutes at 4° C., resuspended in cold buffer and analyzed by flow cytometry.

This assay is based in the fact that intracellular ALDH converts BAAA into the fluorescent compound BAA, which is intracellularly retained because of its net negative charge, which disallows free diffusion. The brightly fluorescent ALDH-expressing cells (ALDH$^+$ cells) were detected in the green fluorescence channel (520-540 nm), as recommended by manufacturer, in a FACS CANTO II (BD Biosciences, San Jose, Calif., USA) and data were analyzed using FACS DIVA software (BD Biosciences) or isolated by FACS ARIA III (BD Biosciences).

Flow Cytometry for Cell Surface Markers Expression

To determine the expression of cell surface proteins, cells were first washed twice with PBS and then resuspended in 100 µL of blocking buffer, prepared by diluting 3% bovine serum albumin (BSA) (Sigma-Aldrich) and 2 mM EDTA in PBS, which blocks possible unspecific junctions of the antibodies with other cell surface proteins. After that, cells were spin down and 10 µL of anti-human antibodies CD44-phycoerithrin (PE) and CXCR4-allophycocyanin (APC) were added to the cell suspension for pancreatic cancer cell lines (Miltenyi Biotec, Auburn, Calif., USA). Incubation with these antibodies was performed for 15 minutes at 4° C. in the dark. Then, cells were centrifuged at 4° C. and resuspended in cold PBS. The brightly fluorescent PE, APC and FITC were detected in the red (564-606 nm), blue (650-670 nm) and green (520-540 nm) fluorescence channels respectively, using a FACS CANTO II and data obtained were analyzed with FACS DIVA software.

Tumorsphere Formation Assay

The ability to generate tumorspheres in low-attachment surfaces under serum depravation conditions, an indicator of the cell self-renewal ability, was carried-out in the enriched CSCs and compared to total population (TP). Briefly, 3×10$^3$ cells per well were then seeded into 6-wells ultra-low attachment plates (Corning Inc., Corning, N.Y., USA) and cultured for 6 days at 37° C. in a humidified incubator with 5% CO$_2$. After that, spheres >75 µM diameter were counted using a Leica DM5500 B fluorescence microscope equipped with Leica CW4000 software (Leica, Soims, Germany), and representative images were taken.

The activity of the MDN-0090 was detected using pancreatic Cancer Stem Cell lines (MiaPaca-2 and BxPC3). For this purpose MTT test was used. Cells were seeded at 10$^6$ cells/well, and treated with the compound during different hours as shown in table 13.

TABLE 13

| MDN-0090 activity on Cancer Stem Cells | | |
|---|---|---|
| | CSCs MiaPaca_2 ED$_{50}$ (µM) | CSCs BxPC3 ED$_{50}$ (µM) |
| MDN-0090_12 hours | 20.8 | 14.29 |
| MDN-0090_24 hours | 14.03 | 17.04 |
| MDN-0090_48 hours | 19.55 | 13.96 |
| MDN-0090_72 hours | 2.18 | 10.35 |

Example 12: Assessment of Antitumor Activity in Xenografts

Figure 3:
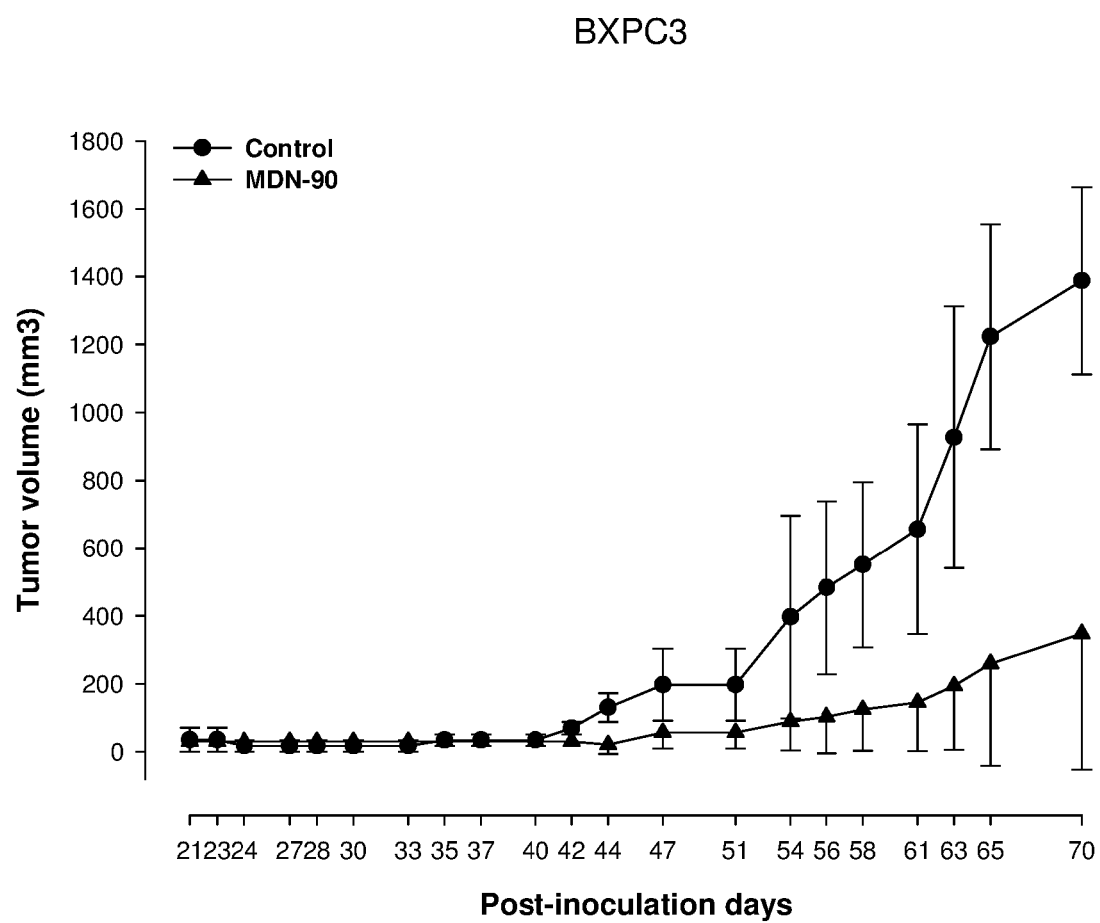
FIG. 3. Results of antitumor activity in xenografts for compound MDN-0090 (tumor volume vs post-incubation days). See example 12.
Figure 3:
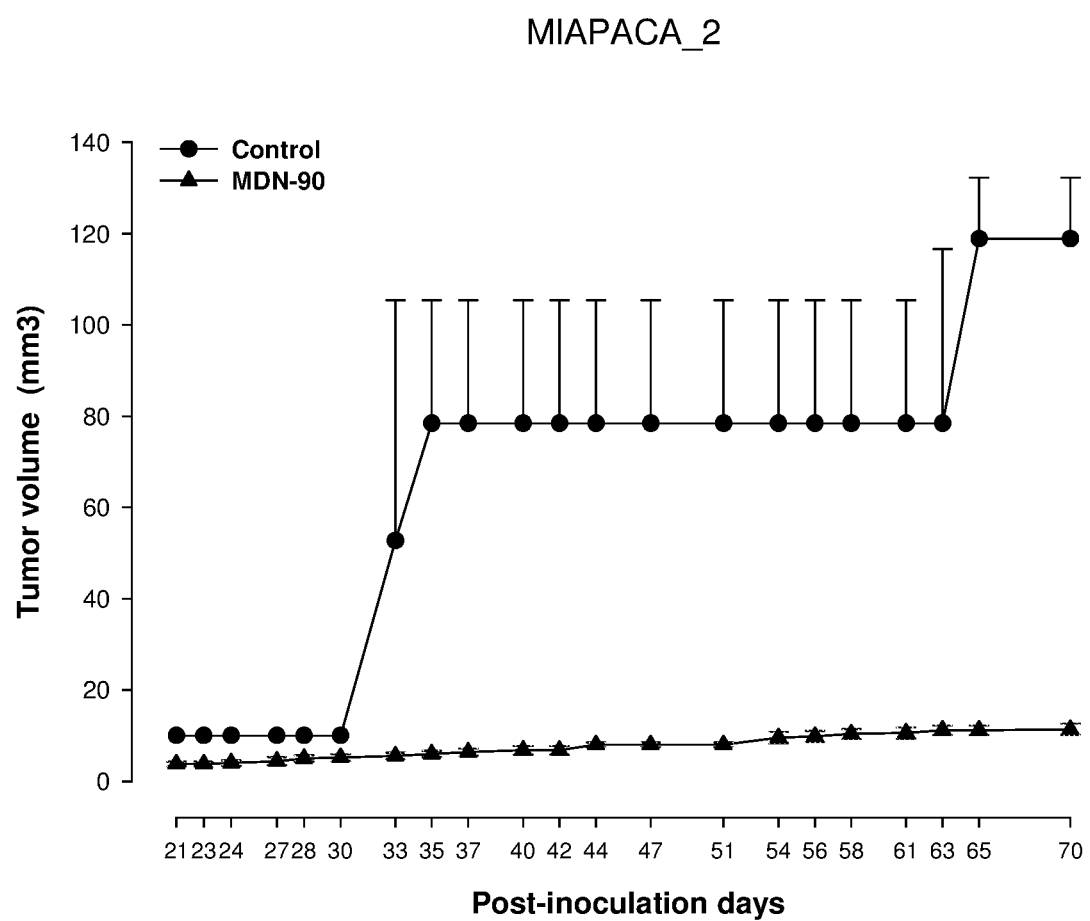

To evaluate the effect of MDN-0090 on tumor growth heterotopic xenografts were used for both BxPC3 and MIAPaca-2 tumor cell lines. Tumor formation was induced by subcutaneous injection of 5×10$^6$ cells/mouse in female NOD scid mice gamma (NOD.Cg-Prkdcscid Il2rgtm1Wjl/SzJ, NSG) of eight weeks old. Animals (n=40, 10 per group) were housed and maintained at 20° C. to 24° C., 50% humidity a light-dark cycle of 14 to 10 h with food and water ad libitum. Tumors were grown to an average volume of 100 mm$^3$, after which they were randomly assigned as control groups (saline) and treated with MDN-0090 (20 mg/kg, dissolved in saline) injected ip three times a week for 50 days. Tumor growth was assessed twice weekly using a digital caliper and the tumor volume was calculated by the formula V=(length)$^2$×width×π/6. Treatment with MDN-0090 reduces the size of tumors as shown in FIG. 3.

Example 13: Assessment of Antitumor Activity Against CSCs

We evaluated the effect of MDN-0090 on CSCs induced tumors. We isolated and characterized the pancreatic CSCs from BxPC3 cell line using the methodology described previously (WO 2016/020572).

In vivo experiment was performed in male and female NOD scid gamma mice (NSG, NOD.Cg-Prkdcscid Il2rgtm1Wjl/SzJ). All animals (n=10 per group) were maintained in a microventilated cage system with a 12-h light/dark cycle, and were manipulated in a laminar air-flow cabinet to keep on the specific pathogen-free conditions.

Figure 4:
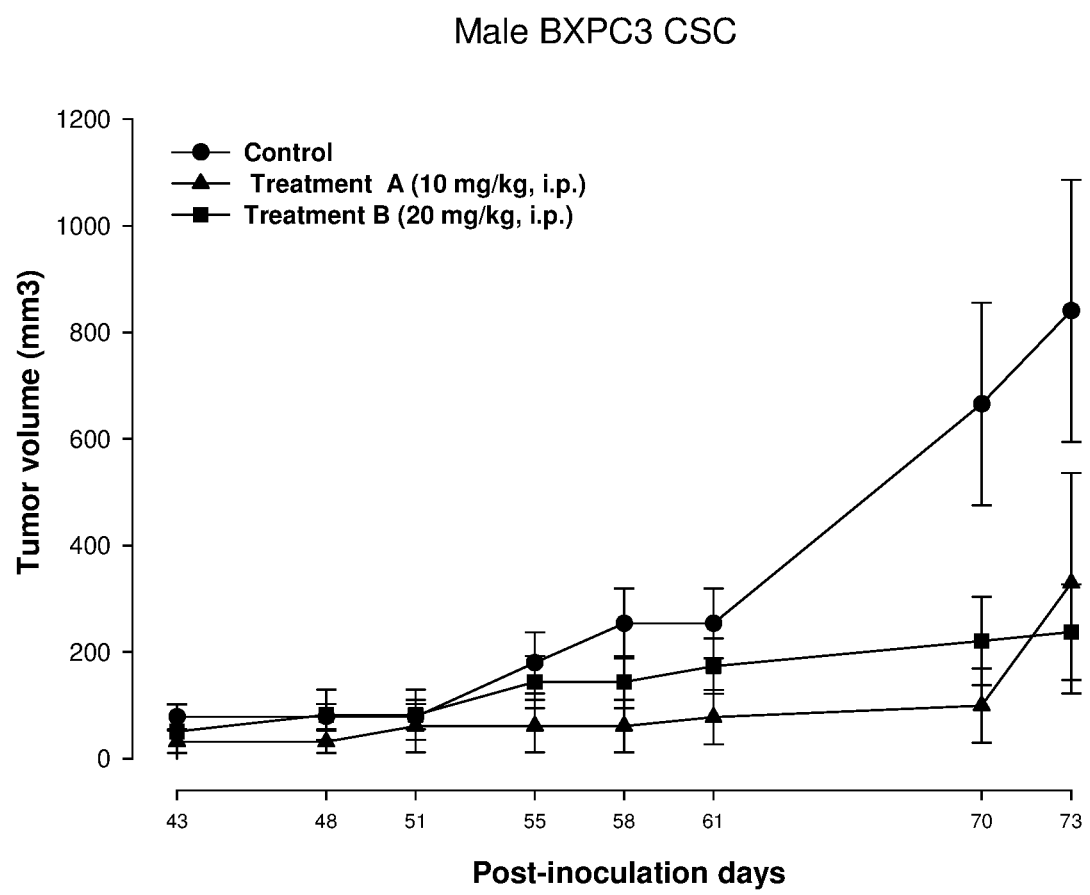
FIG. 4. Results of antitumor activity against CSCs for compound MDN-0090 (tumor volume vs post-incubation days). See example 13.
Figure 4:
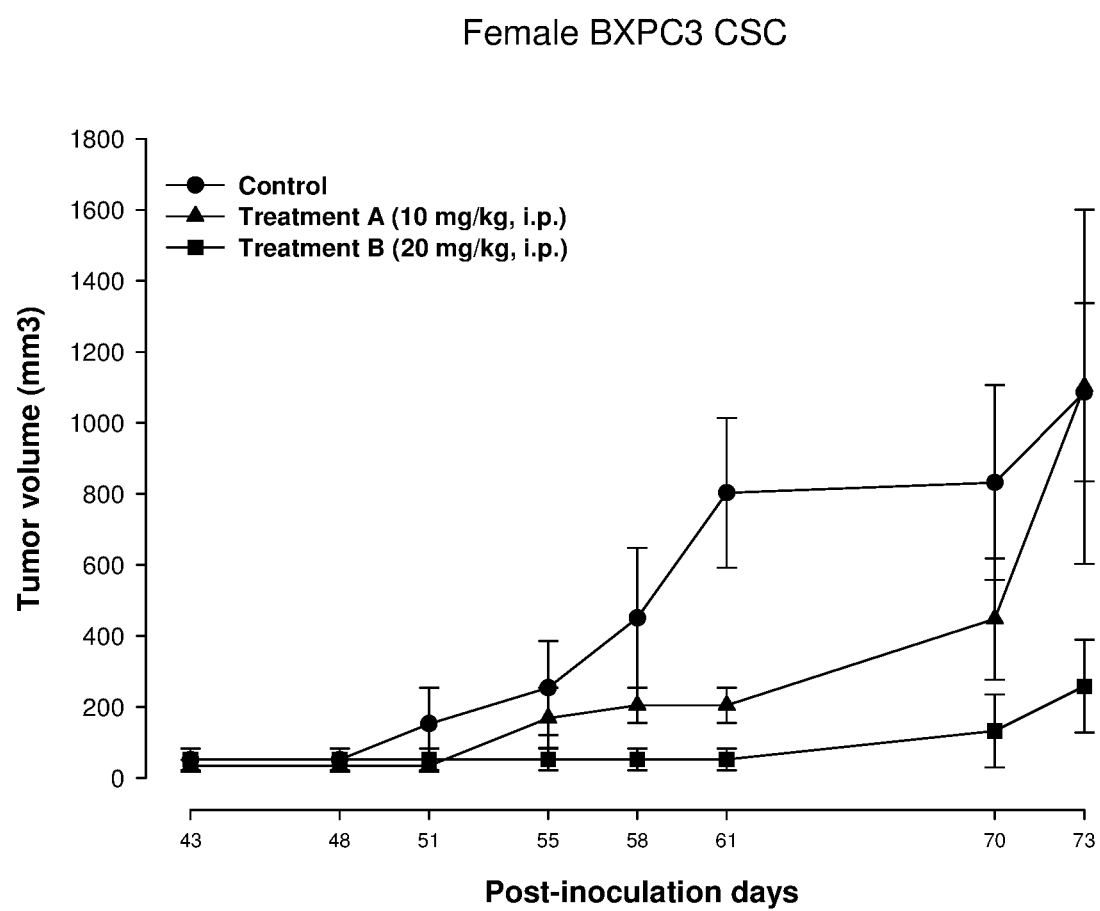

For the induction of xenografts tumors, mice were anesthetized by inhalation of isofluorane, inoculated with $5 \times 10^4$ BxPC3 CSCs by subcutaneously injections into the flank regions. Tumors were grown to an average volume of 100 mm³, after which they were randomly assigned as control groups (saline) and treatment A with MDN-0090 (10 mg/kg, dissolved in saline) and treatment B (20 mg/kg, dissolved in saline) ip three times a week for 52 days. Tumor growth was assessed twice weekly using a digital caliper and the tumor volume was calculated by the formula $V=(length)^2 \times width \times \pi/6$. Treatment with MDN-0090 decreased the size tumor as shown in FIG. 4.

Example 14: Assessment of In Vivo Tumorigenicity Assay

To evaluate the effect of MDN-0090 on the tumorigenicity ability of CSC-like cells heterotopic xenografts using both BxPC3 and MIAPaca-2 tumor cell lines were established. Firstly, we treated cells with MDN-0090 at $IC_{50}$ for 24 hours and after that cells were inoculated into the animals. Pancreatic cancer non-treated cells were used as control.

Figure 5:
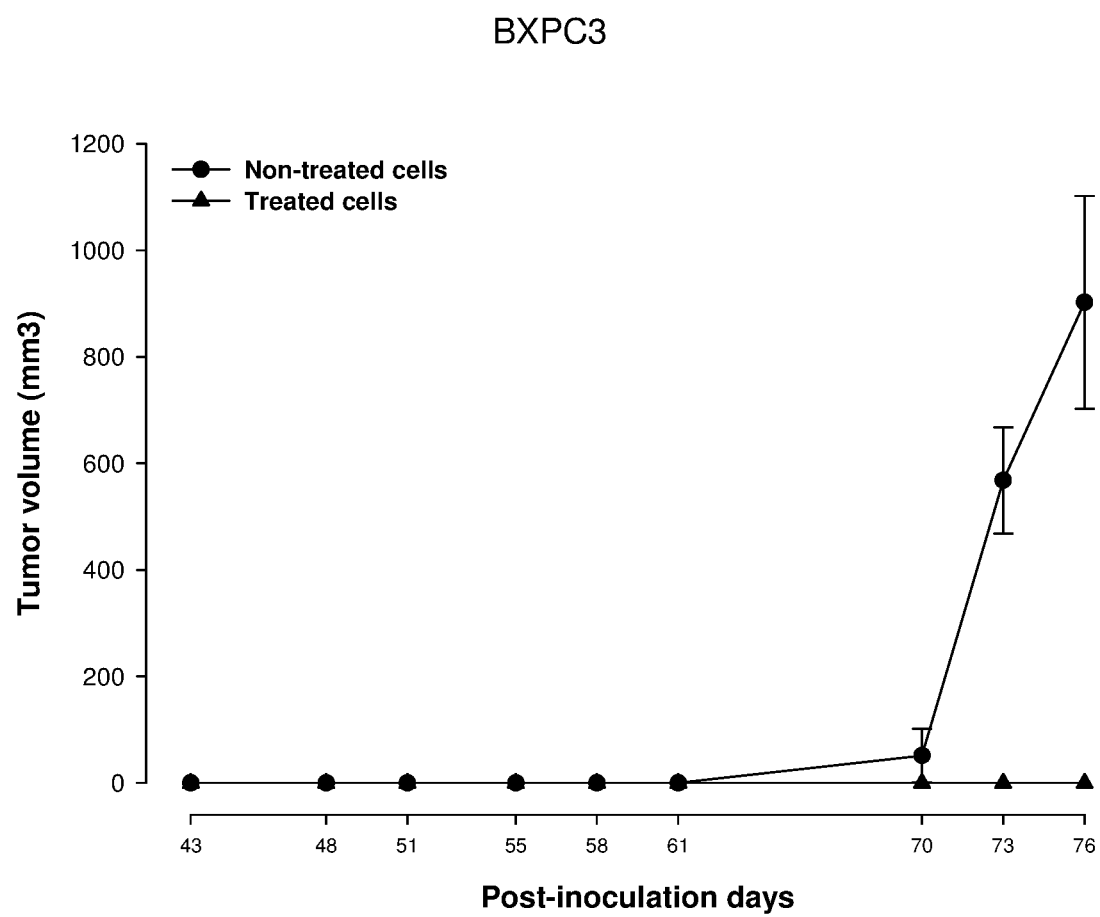
FIG. 5. Results of in vivo tumorigenicity assay for compound MDN-0090 (tumor volume vs post-incubation days). See example 14.
Figure 5:
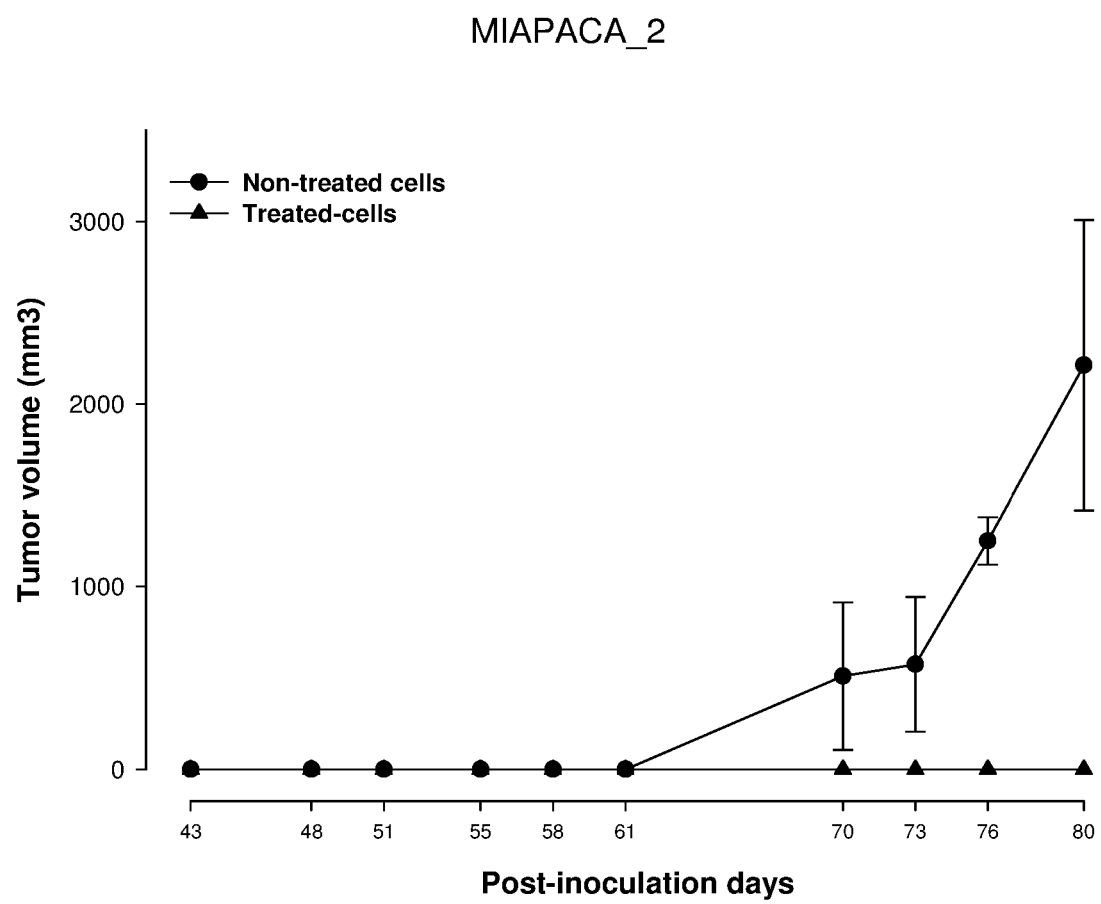

Tumor formation was induced by subcutaneous injection of $1.5 \times 10^4$ in vitro treated or non-treated cells/mouse in NOD scid mice gamma (NOD.Cg-Prkdcscid Il2rgtm1Wjl/SzJ, NSG). Animals (n=20, 10 per group) were housed and maintained at 20° C. to 24° C., 50% humidity a light-dark cycle of 14 to 10 h with food and water ad libitum. We observed the tumor growth every two days. Tumor growth was assessed using a digital caliper and the tumor volume was calculated by the formula $V=(length)^2 \times width \times \pi/6$. Treatment with MDN-0090 reduces tumor formation as shown in FIG. 5.

Example 15: Assessment of Sinergism with Gemcitabine

In order to study if treatment with MDN-0090 could be used in synergism with the most common pancreatic chemotherapic drug (Gemcitabine), MTT assay was performed using tumor cell lines (MiaPaca_2 and BxPC3) and cancer stem cells (MiaPaca_2 and BxPC3). In this way different Gemcitabine concentrations (0.00025-5 μM) were used with MDN-0090 dose response curves (0.39-50 μM) and vice versa. With this assay, we observed that the activity of both compounds (Gemcitabine and MDN-0090) increased when were administered together. (Tables 14-19)

TABLE 14

Dose-response curve of MDN-0090 with different concentration of Gemcitabine on MiaPaca_2

| Treatment | $ED_{50}$ (μM) |
|---|---|
| MDN-0090 + Gemcitabine 5 μM | <0.39 |
| MDN-0090 + Gemcitabine 1.6 μM | <0.39 |
| MDN-0090 + Gemcitabine 0.55 μM | <0.39 |
| MDN-0090 + Gemcitabine 0.18 μM | <0.39 |
| MDN-0090 + Gemcitabine 0.06 μM | <0.39 |
| MDN-0090 + Gemcitabine 0.02 μM | 10.9 |
| MDN-0090 + Gemcitabine 0.0068 μM | 9.4 |
| MDN-0090 + Gemcitabine 0.0023 μM | 13.3 |
| MDN-0090 + Gemcitabine 0.00076 μM | 8.02 |
| MDN-0090 + Gemcitabine 0.00025 μM | 6.9 |

TABLE 15

Dose-response curve of MDN-0090 with different concentration of Gemcitabine on BxPC3

| Treatment | $ED_{50}$ (μM) |
|---|---|
| MDN-0090 + Gemcitabine 5 μM | <0.39 |
| MDN-0090 + Gemcitabine 1.6 μM | <0.39 |
| MDN-0090 + Gemcitabine 0.55 μM | <0.39 |
| MDN-0090 + Gemcitabine 0.18 μM | <0.39 |
| MDN-0090 + Gemcitabine 0.06 μM | <0.39 |
| MDN-0090 + Gemcitabine 0.02 μM | 0.74 |
| MDN-0090 + Gemcitabine 0.0068 μM | 5.46 |
| MDN-0090 + Gemcitabine 0.0023 μM | 2.36 |
| MDN-0090 + Gemcitabine 0.00076 μM | 4.05 |
| MDN-0090 + Gemcitabine 0.00025 μM | 4.00 |

TABLE 16

Dose-response curve of Gemcitabine with different concentration of MDN-0090 on MiaPaca_2

| Treatment | $ED_{50}$ (nM) |
|---|---|
| Gemcitabine + MDN-0090 50 μM | <0.25 |
| Gemcitabine + MDN-0090 25 μM | <0.25 |
| Gemcitabine + MDN-0090 12.5 μM | <0.25 |
| Gemcitabine + MDN-0090 6.25 μM | 22.84 |
| Gemcitabine + MDN-0090 3.125 μM | 32.08 |
| Gemcitabine + MDN-0090 1.56 μM | 26.49 |
| Gemcitabine + MDN-0090 0.78 μM | 23.97 |
| Gemcitabine + MDN-0090 0.39 μM | 31.09 |

TABLE 17

Dose-response curve of Gemcitabine with different concentration of MDN-0090 on BxPC3

| Treatment | $ED_{50}$ (nM) |
|---|---|
| Gemcitabine + MDN-0090 50 μM | <0.25 |
| Gemcitabine + MDN-0090 25 μM | <0.25 |
| Gemcitabine + MDN-0090 12.5 μM | <0.25 |
| Gemcitabine + MDN-0090 6.25 μM | <0.25 |
| Gemcitabine + MDN-0090 3.125 μM | <0.25 |
| Gemcitabine + MDN-0090 1.56 μM | 2.37 |
| Gemcitabine + MDN-0090 0.78 μM | 20.63 |
| Gemcitabine + MDN-0090 0.39 μM | 27.65 |

TABLE 18

Dose-response curve of Gemcitabine with different concentration of MDN-0090 on Cancer Stem Cells MiaPaca_2

| Treatment | IC$_{50}$ (μM) |
|---|---|
| Gemcitabine | 1.9032 |
| Gemcitabine + MDN-0090 0.39 μM | 1.0529 |
| Gemcitabine + MDN-0090 0.78 μM | 0.2370 |
| Gemcitabine + MDN-0090 1.56 μM | 0.1876 |
| Gemcitabine + MDN-0090 3.125 μM | 0.2635 |
| Gemcitabine + MDN-0090 6.25 μM | 0.1113 |
| Gemcitabine + MDN-0090 12.5 μM | 0.2893 |
| Gemcitabine + MDN-0090 25 μM | 0.0289 |
| Gemcitabine + MDN-0090 50 μM | 0.0003 |

TABLE 19

Dose-response curve of MDN-0090 with different concentration of Gemcitabine on Cancer Stem Cells MiaPaca_2

| Treatment | IC$_{50}$ (μM) |
|---|---|
| MDN-0090 + Gemcitabine 0.00025 μM | 2.268801 |
| MDN-0090 + Gemcitabine 0.00076 μM | 2.683225 |
| MDN-0090 + Gemcitabine 0.0023 μM | 2.126558 |
| MDN-0090 + Gemcitabine 0.0068 μM | 2.500001 |
| MDN-0090 + Gemcitabine 0.02 μM | 0.7925277 |
| MDN-0090 + Gemcitabine 0.06 μM | 1.948205 |
| MDN-0090 + Gemcitabine 0.18 μM | 1.78444 |
| MDN-0090 + Gemcitabine 0.55 μM | 0.07812496 |
| MDN-0090 + Gemcitabine 1.6 μM | 0.03906251 |
| MDN-0090 + Gemcitabine 5 μM | 0.03906251 |

LIST OF REFERENCES

Roberts P J, Der C J. (2007). Targeting the Raf-MEK-ERK mitogen-activated protein kinase cascade for the treatment of cancer. Oncogene. May 14; 26(22):3291-310.

Yap, J. L., Worlikar, S., MacKerell, A. D., Shapiro, P. and Fletcher, S. (2011), Small-Molecule Inhibitors of the ERK Signaling Pathway: Towards Novel Anticancer Therapeutics. *Chem Med Chem*, 6: 38-48.

The invention claimed is:

1. A compound of general formula (I) or a pharmaceutically acceptable salt, stereoisomer, or solvate thereof

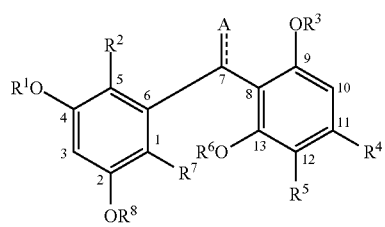

Formula (I)

wherein:

- ---- A represents =O or OH;
- $R^1$ is hydrogen or a hydroxyl protecting group and $R^2$ is selected from the group consisting of:

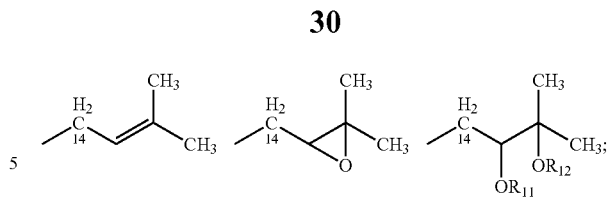

or $R^1$ and $R^2$ together form a ring selected from the group consisting of:

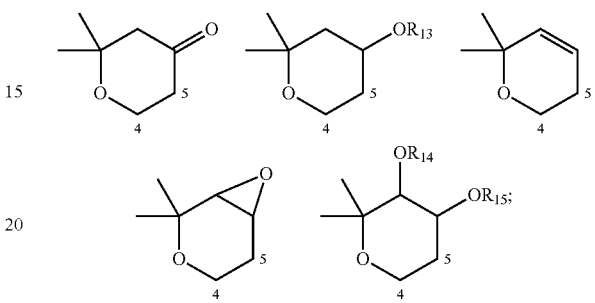

- $R^3$ is hydrogen or a hydroxyl protecting group;
- $R^4$ is methyl;
- $R^5$ is hydrogen or halogen;
- $R^6$ is hydrogen or a hydroxyl protecting group and $R^7$ is CHO or CH$_2$(OH);
- or $R^6$ and $R^7$ together form a single bond;
- $R^8$ is hydrogen or a hydroxyl protecting group;
- $R^{11}$, $R^{12}$, $R^{13}$, $R^{14}$ and $R^{15}$ independently represent hydrogen or a hydroxyl protecting group;
  with the proviso that the compound of general formula (I) is not 2,3',5',6-tetrahydroxy-2'-formyl-6'-(3-methyl-2-butenyl)-4-methyl-benzophenone.

2. The compound according to claim 1, wherein $R^1$ is hydrogen or a hydroxyl protecting group and $R^2$ is

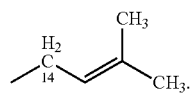

3. The compound according to claim 1, wherein $R^1$ is hydrogen or methyl and $R^2$ is

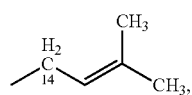

or wherein $R^1$ and $R^2$ together form a ring selected from

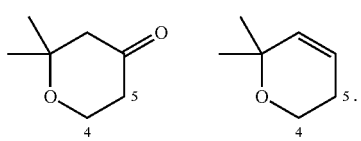

4. The compound according to claim 1, wherein $R^3$ is hydrogen.

5. The compound according to claim 1, wherein $R^5$ is hydrogen or chloro.

6. The compound according to claim 1, wherein $R^6$ is hydrogen and $R^7$ is CHO.

7. The compound according to claim 1, wherein $R^8$ is hydrogen.

8. The compound according to claim 1, wherein hydroxyl protecting groups for $R^1$, $R^3$, $R^6$, $R^8$, $R^{11}$, $R^{12}$, $R^{13}$, $R^{14}$ and $R^{15}$ are independently selected from the group consisting of:

ethers of formula R';

esters of formula —C(=O)R'; and carbonates of formula —C(=O)OR';

wherein R' can be independently selected from the group consisting of substituted or unsubstituted alkyl and substituted or unsubstituted aryl.

9. The compound according to claim 1, which is selected from the group consisting of:

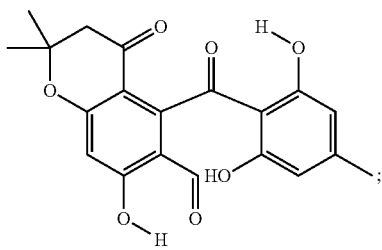

;

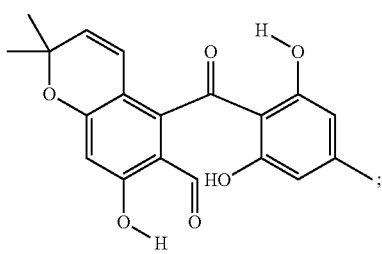

;

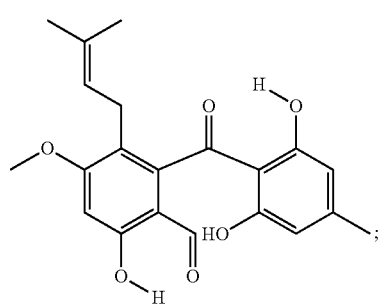

;

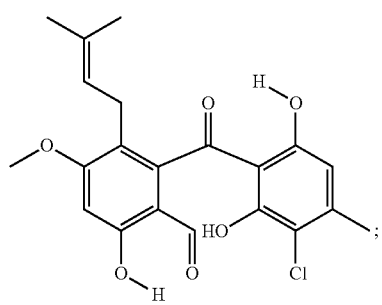

;

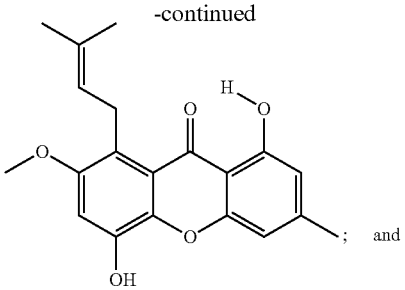

; and pharmaceutically acceptable salts, stereoisomers, or solvates thereof.

10. A pharmaceutical composition comprising an effective amount of at least one compound of formula (I) or a pharmaceutically acceptable salt, stereoisomer or solvate thereof Formula (I)

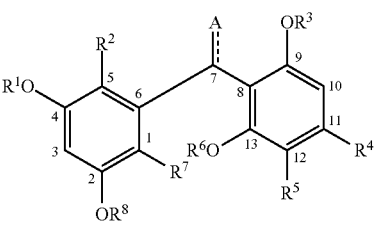

wherein:

═ A represents =O or OH;

$R^1$ is hydrogen or a hydroxyl protecting group and $R^2$ is selected from the group consisting of:

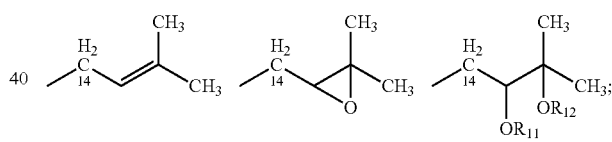

or $R^1$ and $R^2$ together form a ring selected from the group consisting of:

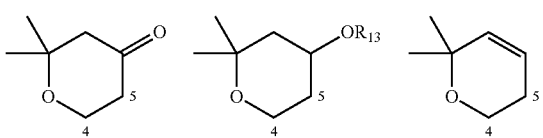

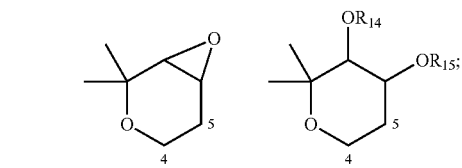

;

$R^3$ is hydrogen or a hydroxyl protecting group;

$R^4$ is methyl;

$R^5$ is hydrogen or halogen;

$R^6$ is hydrogen or a hydroxyl protecting group and $R^7$ is CHO or CH$_2$(OH);

or $R^6$ and $R^7$ together form a single bond;

$R^8$ is hydrogen or a hydroxyl protecting group;

$R^{11}$, $R^{12}$, $R^{13}$, $R^{14}$ and $R^{15}$ independently represent hydrogen or a hydroxyl protecting group;

and a pharmaceutically acceptable excipient;

said effective amount being effective for treatment of cancer;

with the proviso that the compound of formula (I) is not 2,3',5',6-tetrahydroxy-2'-formyl-6'-(3-methyl-2-butenyl)-4-methyl-benzophenone.

11. The pharmaceutical composition according to claim 10, wherein the compound of formula (I) is selected from the group consisting of:

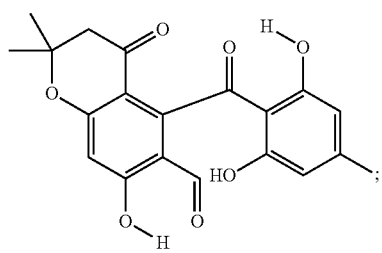

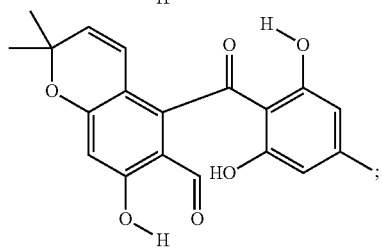

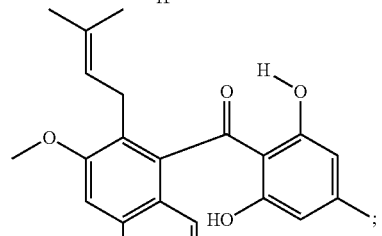

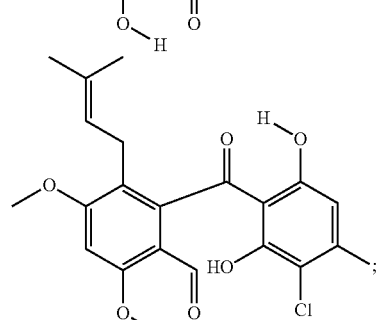

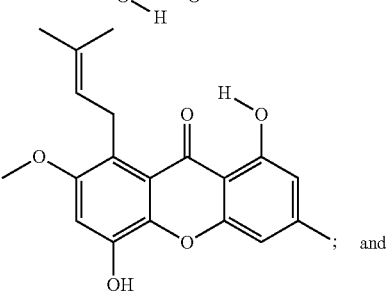
; and pharmaceutically acceptable salts, stereoisomers, or solvates thereof.

12. A method for the manufacture of a medicament comprising the step of combining a compound of claim 1, with a pharmaceutically acceptable excipient.

13. A method for the treatment of cancer, the method comprising administering to the subject in need of such a treatment an effective amount of the pharmaceutical composition of claim 10.

14. The method according to claim 13, wherein, in the compound of formula (I), $R^1$ is hydrogen or a hydroxyl protecting group and $R^2$ is

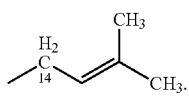

15. The method according to claim 13, wherein, in the compound of formula (I), $R^1$ is hydrogen or methyl and $R^2$ is

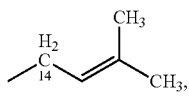

or wherein $R^1$ and $R^2$ together form a ring selected from the group consisting of:

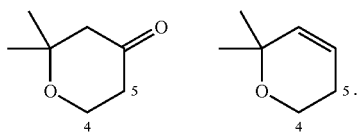

16. The method according to claim 14, wherein the compound of formula (I) meets at least one of the following conditions (a) to (d):
(a) $R^3$ is hydrogen;
(b) $R^5$ is hydrogen or chloro;
(c) $R^6$ is hydrogen and $R^7$ is CHO; and
(d) $R^8$ is hydrogen.

17. The method according to claim 15, wherein the compound of formula (I) meets at least one of the following conditions (a) to (d):
(a) $R^3$ is hydrogen;
(b) $R^5$ is hydrogen or chloro;
(c) $R^6$ is hydrogen and $R^7$ is CHO; and
(d) $R^8$ is hydrogen.

18. The method according to claim 13, wherein the compound of formula (I) is selected from the group consisting of:

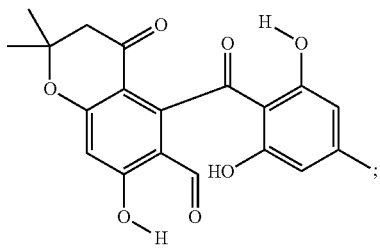

-continued

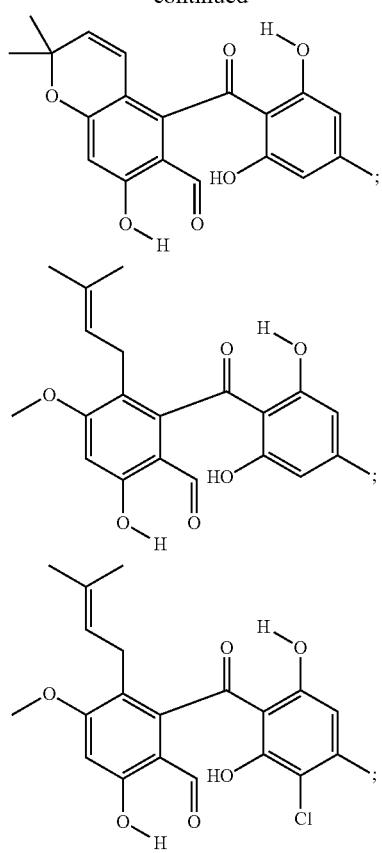

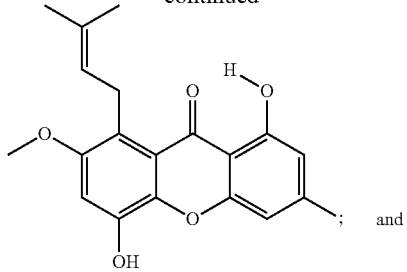

pharmaceutically acceptable salts, stereoisomers, or solvates thereof.

19. A process for obtaining a compound of general formula (I) of claim 1 or a pharmaceutically acceptable salt, stereoisomer or solvate thereof, said process comprising the steps of cultivating a strain of *Onychocola* sp. deposited at the CBS with accession number CBS 139230 in an aqueous nutrient medium with assimilable carbon and nitrogen sources and salts, under controlled submerged aerobic conditions, and then recovering and purifying the compound of general formula (I) from the culture broth.

20. A method for the treatment of cancer, the method comprising administering to a subject in need of such treatment an effective amount of a compound of formula (I) of claim 1 or a pharmaceutically acceptable salt, stereoisomer or solvate thereof.

21. A pharmaceutical composition comprising:
　at least one compound of formula (I) of claim 1, or a pharmaceutically acceptable salt, stereoisomer, or solvate thereof; and
　a pharmaceutically acceptable excipient.

* * * * *